United States Patent [19]

Zamarron et al.

[11] Patent Number: 5,372,933
[45] Date of Patent: Dec. 13, 1994

[54] POLYPEPTIDES THAT MIMIC RECEPTOR-INDUCED BINDING SITES, AND METHODS OF USING SAME

[75] Inventors: Concepcion Zamarron; Edward F. Plow; Mark H. Ginsberg, all of San Diego, Calif.

[73] Assignee: The Scripps Research Institute, La Jolla, Calif.

[21] Appl. No.: 654,839

[22] Filed: Feb. 12, 1991

Related U.S. Application Data

[63] Continuation-in-part of Ser. No. 252,753, Oct. 3, 1988, abandoned, and a continuation-in-part of Ser. No. 415,029, Sep. 29, 1989, abandoned.

[51] Int. Cl.$^5$ .................. A61K 37/02; C07K 7/08; C07K 7/10; G01N 33/543
[52] U.S. Cl. .................. 435/7.21; 435/13; 436/518; 514/12; 514/13; 514/14; 530/324; 530/325; 530/326; 930/DIG. 811; 930/DIG. 821
[58] Field of Search .................. 435/7.21, 7.24, 7.94, 435/13; 436/518, 824, 547, 548; 514/12, 13, 14; 530/324, 325, 326, 327, 413, 830; 930/DIG. 811, DIG. 821

[56] References Cited

U.S. PATENT DOCUMENTS 4,455,290 6/1984 Olexia et al. .................. 424/1.1

OTHER PUBLICATIONS

M. Kloczewiak et al., *Biochemistry*, 23, 1767–1774, 1984.
P. A. W. Edwards, *Biochem. Jour.*, 200, 1–10, 1981.

*Primary Examiner*—David Saunders
*Attorney, Agent, or Firm*—April C. Logan

[57] ABSTRACT

Receptor-induced binding sites (RIBS) expressed in a ligand when that ligand is bound in a complex with a receptor are disclosed, as are polypeptides that correspond in amino acid residue sequence with a RIBS expressed by a receptor-ligand complex. Particularly-preferred polypeptides correspond to a RIBS amino acid sequence of the gamma chain of human fibrinogen. Monoclonal antibodies that immunoreact with a RIBS but do not substantially immunoreact with either the ligand or the receptor when free in solution are also disclosed, as are hybridomas secreting those antibodies, and methods of making and using such antibodies.

13 Claims, 2 Drawing Sheets

POLYPEPTIDES THAT MIMIC RECEPTOR-INDUCED BINDING SITES, AND METHODS OF USING SAME

This invention was made with the support of the United States Government, and the United States Government has certain rights in the invention pursuant to National Institutes of Health Contract HL-16411.

CROSS REFERENCE TO RELATED APPLICATIONS

This is a continuation-in-part application of copending applications Ser. No. 252,753, filed Oct. 3, 1988 and Ser. No. 415,029, filed Sep. 29, 1989.

TECHNICAL FIELD

The present invention relates to an antibody binding site that is induced on a ligand when that ligand is bound by a receptor to form a receptor-ligand complex. Monoclonal antibodies that immunoreact with such receptor-induced binding site as well as associated therapeutic and diagnostic methods are also contemplated.

BACKGROUND

Interactions of ligands with cell surface receptor molecules are hallmarks of biological processes. Exemplary of such interactions are the binding of the ligand formed by a portion of the envelope protein (gp140) of the AIDS virus (HIV) with the CD4 receptor on T cells, the receptors of the major histocompatibility complex that interact with numerous ligands in the processes of self/non-self discrimination in the immunological system, and the interaction of the fibrinogen ligand with the GPIIb-IIIa cellular receptor on platelets. The fibrinogen:GPIIb-IIIa ligand-receptor pair are of particular interest in blood clotting, thrombus formation, and are utilized hereinafter as exemplary of ligands and receptors.

The art has long sought immunological methods to distinguish the bound and non-bound forms of ligands and receptors because that ability would allow for a determination of the state of the physiological mechanisms mediated by receptor:ligand complex formation. Until recently, efforts to make such determinations by immunological methods have been frustrated because biological samples can contain ligands and receptors in both bound (complexed) and free forms.

For instance, the vasculature of individuals undergoing a thrombotic event contains non-bound forms of fibrinogen and GPIIb-IIIa as well as platelets having a fibrinogen:GPIIb-IIIa complex on their surface. The fibrinogen:GPIIb-IIIa complex expresses antigenic determinants common to non-bound fibrinogen and non-bound GPIIb-IIIa, thus making it difficult to identify a thrombotic condition or thrombus location by existing immunological methods.

Recently, Frelinger et al., *J. Biol. Chem.*, 263:12397–12402 (1988) reported identifying an antigenic determinant expressed by GPIIb-IIIa only when GPIIb-IIIa was bound to a ligand. That is, the antigenic determinant described by Frelinger et al. was expressed by the receptor of the receptor:ligand complex.

Others have reported the preparation of monoclonal antibodies that immunoreact with an antigenic determinant expressed upon ligand binding to artificial, non-receptor surfaces. Sofia et al., *J. Colloid Interface Sci.*, 107:204–208 (1985) describe a particular monoclonal antibody, referred to as $DSB^2$, induced by immunization with cross-linked fibrin fragment which binds to plastic-adsorbed fibrinogen and also to the so-called fibrinogen D fragment adsorbed on plastic or free in solution. Reportedly, the antibody does not bind to solution phase fibrinogen or the so-called fibrinogen E fragment when in solution.

Additionally, Nilsson et al., *Molec. Immunol.*, 24:487–94 (1987), report the preparation of monoclonal antibodies that immunoreact with complement C3 fragments particle-bound to Zymosan A, but not with soluble C3 fragments. The nature of protein binding to Zymosan A involves covalent chemical bonds.

In another report Abrams et al., *Blood (Suppl.* 1), 70:355a (December 1987) briefly discuss a monoclonal antibody designated 9F9 that is said in the published abstract to bind to platelet-bound fibrinogen. That brief report, however, does not characterize tile specific binding properties of monoclonal 9F9.

Numerous monoclonal antibodies that immunoreact with solubilized fibrinogen have been reported. One such report is Lindon et al., *Blood*, 68:355–362 (Audi. 1988). That paper reported the use of commercially available anti-human fibrinogen monoclonal antibodies as well as affinity-purified polyclonal antibodies to the D and E fragments.

BRIEF SUMMARY OF THE INVENTION

The present invention involves the discovery that ligands specifically bound to a receptor can be distinguished from non-bound ligands by the presence of a receptor-induced antibody binding site (RIBS) expressed by the receptor-bound ligand. That is, a class of antigenic determinants has now been discovered in which a determinant is expressed when a ligand specifically binds to a receptor but not when the receptor and ligand are not bound.

A RIBS is expressed on a ligand due to the specific interaction of a ligand binding to its cognate receptor. A RIBS is not an antigenic determinant site that is exposed when a protein interacts non-specifically with another surface, such as plastic-absorbed protein, or when a protein interacts by covalent chemical bonds with a surface. These latter two examples are disclosed in the Soria et al., and Nilsson et al., references described above, and do not involve a specific receptor ligand binding interaction that generates a RIBS as defined herein.

Also contemplated by the present invention are antibody molecules that immunoreact with a ligand when it is bound to a receptor, but do not immunoreact with either the receptor or ligand when they are not specifically bound to each other. In a preferred embodiment, an antibody of the invention recognizes a RIBS localized on human fibrinogen.

Such antibodies recognize a RIBS induced as a consequence of the fibrinogen interaction with a receptor, therefore, preferably GPIIb-IIIa on platelets. An antibody of this invention immunoreacts selectively with bound fibrinogen, even in the presence of a large excess of plasma fibrinogen. The unique properties of these antibodies thereby afford a wide variety of diagnostic systems and therapeutic methods of use.

A preferred embodiment of the present invention is for a monoclonal antibody that immunoreacts with a receptor-induced binding site expressed by a receptor ligand complex. Preferably the monoclonal antibody is selected from the group consisting of antibodies designated 2G5, 2F10, 3G11, and 4G10. The nonoclonal antibody is produced by a hybridoma selected from the group consisting of hybridoma 2G5, hybridoma 2F10, hybridoma 3G11, and hybridoma 4G10.

Another embodiment of this invention is a cell culture composition which comprises:
a) a hybridoma that produces an antibody that immunoreacts with a receptor-induced binding site expressed by a GPIIb-IIIa:fibrinogen complex, the hybridoma selected from the group consisting of hybridoma 2G5, hybridoma 2F10, hybridoma 3G11 and hybridoma 4G10;
b) antibody molecules secreted by the hybridoma; and
c) a culture medium for the hybridoma.

Further contemplated is a method of detecting the presence of a receptor-ligand complex wherein the system comprises a monoclonal antibody that immunoreacts with a receptor-induced binding site (RIBS) expressed by a receptor-ligand complex, which RIBS is not expressed by the non-bound receptor or the non-bound ligand. Preferably the receptor complex is GPIIb-IIIa:fibrinogen. Also preferred is a method wherein the monoclonal antibody is linked to an in vivo indicating means.

Another aspect of this invention is a diagnostic system, in kit form, for the assay in a vascular fluid sample for the presence of the GPIIb-IIIa:fibrinogen complex in which the diagnostic system comprises a monoclonal antibody that immunoreacts with a RIBS expressed by this complex.

Another embodiment of this invention is for a method of dispersement of a thrombus, in vivo, in a mammal which comprises:
a) intravenously administering to said mammal an effective amount of a monoclonal antibody-plasminogen activating enzyme conjugate wherein the monoclonal antibody region of the conjugate immunoreacts with a RIBS expressed by a GPIIb-IIIa:fibrinogen complex. Preferably the plasminogen activating enzyme is tissue plasminogen activator and the monoclonal antibody is selected from the group consisting of 2G5, 2F10, 3G11, and 4G10.

Another aspect of the present invention is for the in vivo detection of a thrombus in a mammal which comprises the steps of:
a) intravenously administering to a mammal an effective amount of a monoclonal antibody that immunoreacts with a RIBS expressed by a GPIIb-IIIa:fibrinogen complex indicative of a thrombus;
b) maintaining the administered mammal for a predetermined time period sufficient for the monoclonal antibody to immunoreact with the GPIIb-IIIa:fibrinogen complex to form an immunoreaction product thereof; and
c) assaying for the presence of any immunoreaction product formed in step (b) and thereby the presence of the thrombus.

Also contemplated is a polypeptide that corresponds in amino acid residue sequence with an instant RIBS expressed by a receptor-ligand complex. In a preferred embodiment the polypeptide contains an amino acid residue sequence that corresponds to a RIBS on a GPIIb-IIIa-fibrinogen complex. More preferably, the entire sequence of the polypeptide is identical to the corresponding RIBS amino acid sequence of the gamma chain of human fibrinogen. A particularly preferred polypeptide comprises up to about 40 amino acid residues and includes an amino acid residue sequence having the formula (SEQ ID NO: 1)

Lys-Thr-Arg-Trp-oTyr-Ser-Met-Lys-Lys-Thr-Thr-Met-Lys.

Most preferably, the polypeptide has the formula (SEQ ID NO: 1):

H-Lys-Thr-Arg-Trp-Tyr-Ser-Met-Lys-Lys-Thr-Thr-Met-Lys-OH.

The present invention also is for an antibody that immunoreacts with an instant polypeptide which mimics a RIBS epitope on the ligand molecule of a receptor-ligand complex, e.g., as when the polypeptide is immobilized on a surface. Preferably, an antibody of the invention also immunoreacts with a a receptor-ligand complex containing an amino acid residue sequence corresponding to that for the polypeptide. A particularly preferred antibody in this regard is secreted by the hybridoma 2G5, having the ATCC designation HB9847.

The instant polypeptides and antibodies afford a number of therapeutic and diagnostic protocols. For example, a method is contemplated for inhibiting and/or neutralizing an instant antibody from immunoreacting with a receptor-ligand complex in a patient by treating the patient with an instant polypeptide, as when admixed with a pharmaceutically acceptable excipient. Thus, a polypeptide as described above competitively immunoreacts with the antibody, thereby reducing the presence of free antibody in the patient.

Another method of use contemplated for the instant polypeptides and antibodies is for detecting the presence of antibody in a solution containing the antibody. Thus, the solution can be passed over a surface having an instant polypeptide immobilized thereon, with the antibody preferentially reacting with the polypeptide to form a detectible immunocomplex. The presence of immunocomplex indicates the presence of antibody in the solution.

A further use contemplated is for isolating an instant antibody from a solution containing the antibody, e.g., from impurities in the solution. The antibody-containing solution can be passed over an instant polypeptide immobilized on a surface, from which the antibody is subsequently displaced. The target antibody is collected and thereby purified.

DESCRIPTION OF THE DRAWINGS

FIG. 2A, chromatogram monitored by absorbance at 280 nm and indicating the fall-through (F) and bound (B) fractions. Bound material was pooled and was subjected to HPLC (high pressure liquid chromatography) on a reverse phase Vydac C18 column. FIG. 2B, HPLC chromatogram at 280 nm.

DETAILED DESCRIPTION OF THE INVENTION

A. Definitions

Figure 1:
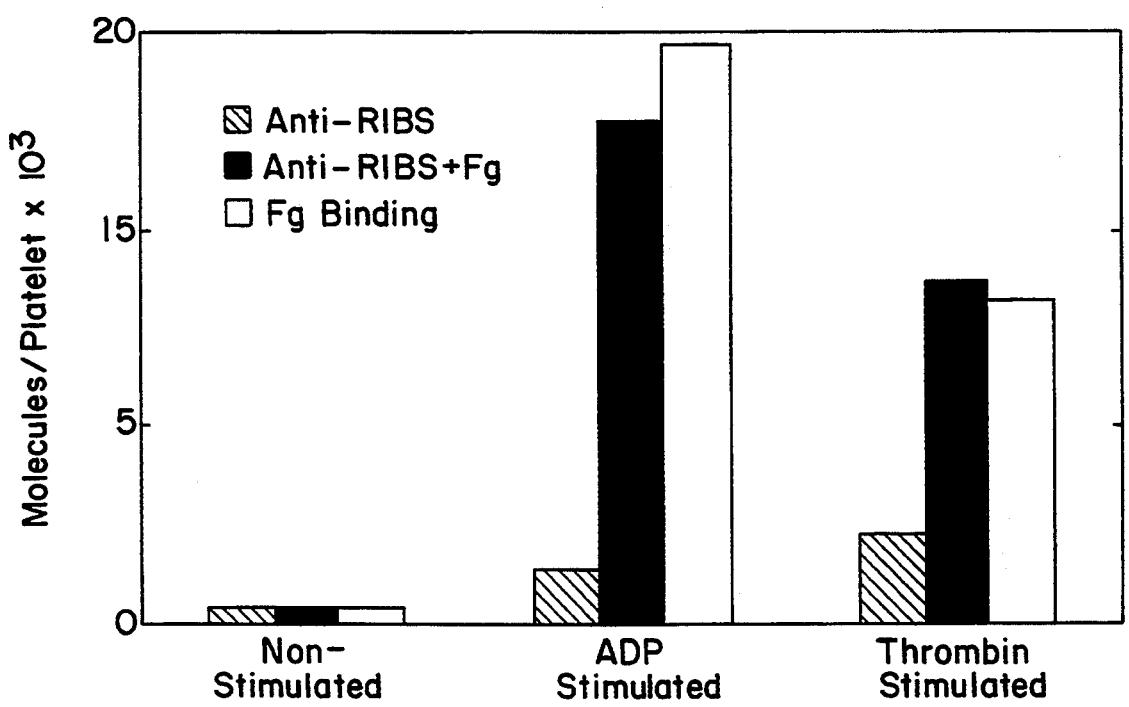
FIG. 1 depicts binding of MAb 2G5 to platelet-bound fibrinogen. Binding of $^{125}I$-2G5 (0.1 $\mu M$) to platelets ($1 \times 10^8$/ml) was performed with nonstimulated, ADP (10 $\mu M$) stimulated or $\alpha$-thrombin (0.5 units/ml) stimulated platelets, in the absence (hatched bar) or in the presence (solid bar) of a 1 $\mu M$ fibrinogen. In parallel experiments, binding of $^{125}I$-fibrinogen (0.3 $\mu M$) alone was measured (open bar).

Amino Acid Residue Sequence: a series of two or more amino acid residues joined via peptide linkages between adjacent residues to form a peptide or polypeptide. An amino acid residue sequence is conveniently represented by the one or three letter abbreviations for its constituent amino acids. The abbreviations used herein for amino acids are those provided at 37 C.F.R. §1,822(b)(2) and are reproduced in the following Table of Correspondence:

| TABLE OF CORRESPONDENCE | | |
|---|---|---|
| ABBREVIATION | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unspecified |

The individual residues comprising an amino acid residue sequence herein may be in the D or L isomeric form as long as the desired functional property is retained by molecule(s) incorporating the amino acid residue sequence. Also, the amino acid residue sequence may include post-translationally modified amino acids, e.g., hydroxylated, glycosylated amino acid residues, or residues linked via disulfide bonds. In addition, an amino acid residue sequence can include one or more modified or unusual amino acids, such as those listed in 37 C.F.R. §1.822(b)(4), which are incorporated herein by reference. An amino acid residue sequence can be represented by the abbreviations corresponding to its constituent amino acids in which a hyphen between two adjacent abbreviations indicates a peptide linkage between the corresponding residues.

Peptide/Polypeptide: a polymer comprising at least two amino acid residues in which adjacent residues are connected by a peptide bond between the alpha-amino group of one residue and the alpha-carbonyl group of an adjacent residue. The primary structure of a polypeptide has a primary amine group at one terminus and a carboxylic acid group at the other terminus of the polymer. Thus, a polypeptide may be represented by the formula:

$$H-[NH-CH-C(O)]_i-OH$$
$$\phantom{H-[NH-}\mid$$
$$\phantom{H-[NH-C}R$$

where R is a side chain characteristic of a given amino acid residue and i indicates the number of amino acid residues comprising the polymer which number is two or more. A polypeptide can comprise one or more amino acid residue sequences. Also, a polypeptide in aqueous solution is usually in one or more zwitterionic forms depending on the pH of the solution.

Protein: a single polypeptide or set of cross-linked polypeptides comprising more than about 50 amino acid residues. Proteins can have chemical crosslinking, i.e., via disulfide bridges, within the same polypeptide chain or between adjacent polypeptides. Proteins can be glycosylated in which case they are called glycoproteins.

Receptor: A biologically active proteinaceous molecule that specifically binds to (or with) other molecules, referred to as ligands, to form a receptor-ligand protein or glycoprotein complex.

Ligand and Cognate Ligand: A molecule that contains a structural portion that is bound by specific interaction with a particular receptor molecule.

Antigenic Determinant or Antigen: Antigenic determinant or antigen refers to the actual structural portion of the antigen that is immunologically bound by an antibody combining site. The terms are also used interchangeably with epitope.

Neo-antigen: A neo-antigen, as defined herein, is a new antigenic determinant that is not expressed by a ligand prior to binding to the receptor but which is expressed in the ligand-receptor complex.

Cryptic Antigenic Determinant: Refers to a neo-antigenic determinant formed by changes in conformation of a ligand protein upon binding to its cognate (specific) receptor. Thus, a ligand described herein does not express a cryptic antigenic determinant unless the ligand has specifically bound to a receptor.

Receptor-induced Binding Site (RIBS): A RIBS is a neo-antigenic determinant that is expressed by the ligand portion of a receptor-ligand complex but is not expressed by either the non-bound ligand or the non-occupied receptor. A RIBS can be either "conformational" or "sequential" A RIBS is the result of specific alterations of the ligand induced by receptor binding, i.e., a "cryptic antigenic determinant".

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: The phrase monoclonal antibody in its various grammatical forms refers to a population of antibody molecules that contains essentially only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

B. Receptor-Induced Binding Sites and Polypeptides

As noted earlier, ligand-receptor complex formation lies at the heart of many biological processes. It has now been found that along with the biological function that accompanies ligand-receptor formation, another, more subtle change occurs. The change is in the conformation of the ligand molecule that results from the binding interaction with the receptor upon complex formation. The change in ligand conformation results in the formation of a neo-antigenic determinant that is expressed substantially only upon formation of the complex. The neo-antigenic determinant is referred to herein as a receptor-induced binding site (RIBS).

The RIBS expressed by the complex formed by the binding of fibrinogen as ligand to GPIIb-IIIa as receptor is used illustratively herein as exemplary of the RIBS-forming phenomenon. Monoclonal antibodies that immunoreact with the fibrinogen-GPIIb-IIIa complex but do not substantially react with either the ligand or receptor when not present as a fibrinogen-GPIIb-IIIa complex are also utilized herein as exemplary of anti-RIBS (or more simply, RIBS) monoclonal antibodies.

In addition to the exemplary RIBS and RIBS monoclonal antibodies specifically discussed herein, several additional ligand-receptor complexes are reported in the literature. The present invention contemplates theft such complexes also form RIBS and monoclonal antibodies can be raised to those RIBS, using the techniques described herein. Such monoclonal antibodies immunoreact with only the ligand portion of the ligand-bound receptor complex and not with the free receptor or free ligand. Using such RIBS monoclonals, one can now assay for the presence and amount of a ligand-receptor complex, i.e., an occupied receptor or occupied ligand, in the presence of either or both of the free ligand and free receptor.

Exemplary pairs of RIBS-forming ligands and receptors are enumerated in Table 1 that follows. These pairs are intended to be merely illustrative and not limiting of the receptor-ligand combination that can form an instant RIBS.

TABLE 1

| LIGAND RECEPTOR PAIRS | | |
|---|---|---|
| Ligand | Receptor | Citation No. |
| Von Willebrand Factor | GPIIb-IIIa | 1 |
| Vitronectin | GPIIb-IIIa | 1 |
| Fibronectin | Fibronectin Receptor | 1 |
| ICAM-1 | LFA-1 | 1 |
| Laminin | CSAT | 2 |
| Collagen | VLA-2 | 3 |
| C3bi | CR3 Complement Receptor | 4 |
| C3d | CR2 Complement Receptor | 5 |
| HIV-gp140 | CD4 T Cell | 6 |

TABLE 1-continued

| LIGAND RECEPTOR PAIRS | | |
|---|---|---|
| Ligand | Receptor | Citation No. |
| FSH Releasing Protein | FRP Receptor | 7 |
| Apo B-100 | Apolipoprotein Receptor | 8 |
| IL-2 | Interleukin Receptor | 9 |
| Immunoglobulins | Fc Receptor | 10 |
| Chorionic Gonadotrophin | Somatostatin Receptor | 11 |
| PDGF | PDGF Receptor | 12 |
| Transferrin | Transferrin Receptor | 13 |

1 Ruoslahti et al., Science, 238:491–497 (1987).
2 Horwitz et al., J. Cell. Biol., 101:2134 (1985).
3 Nieuwenhuis et al., Nature, 318:470 (1985).
4 Wright et al., PNAS, 84:1965 (1987).
5 Nemerow et al., J. Virol., 55:347 (1985).
6 Guyader et al., Nature, 320:662 (1987).
7 Yu et al., Nature, 330:765 (1987).
8 Yamada et al., J. Clin. Invest., 80:507 (1987).
9 Dower et al., Immunol. Today, 8:46 (1987).
10 Anderson et al., J. Immunol, 138:2254 (1987).
11 Kim et al., J. Biol. Chem., 262:470 (1987).
12 Keating et al., J. Biol. Chem, 252:7932 (1987).
13 Kohgo et al., Blood, 70:1955 (1987).

In one embodiment of the invention, a polypeptide is contemplated that mimics an epitope of the ligand in a receptor-ligand complex at a RIBS on the ligand. Accordingly, an instant polypeptide has an amino acid residue sequence that corresponds with that of the ligand in the region of the RIBS.

In a preferred embodiment, a polypeptide contains an amino acid residue sequence that corresponds to an amino acid residue sequence on the gamma chain of human fibrinogen which defines a RIBS. Most preferably, the entire sequence of the polypeptide will be identical with that of the fibrinogen region which it mimics, however, conservative substitutions of the polypeptide from that for native fibrinogen are also contemplated.

Thus, in a preferred aspect of the invention, a polypeptide of this invention has an amino acid residue sequence represented by the following formula:

$$H-X_n-Y-X_m-OH$$

where Y is an amino acid residue sequence selected from the group of human gamma chain fibrinogen amino acid residue sequences; $X_n$ is absent when n=0 and is an N-terminal (leader segment) amino acid residue sequence containing up to about 30 residues when n=1; and $X_m$ is absent when m=0 and is a C-terminal (tail segment) amino acid residue sequence containing up to about 30 residues when m=1.

The entire polypeptide comprises up to about 40 amino acid residues, more preferably up to about 30 residues, and most preferably, up to about 20 residues.

Preferably, Y corresponds with an amino acid residue sequence on the gamma chain of human fibrinogen from about residue 363 to about residue 393. More preferably, Y has an amino acid residue sequence given by the formula (SEQ ID NO: 2): Asn-Gly-Ile-Ile-Trp-Ala-Thr-Trp-Lys-Thr-Arg-Trp-Tyr-Ser-Met-Lys-Lys-Thr-Thr. Most preferably, Y has the formula (SEQ ID NO: 1) Lys-Thr-Arg-Trp-Tyr-Ser-Met-Lys-Lys-Thr-Thr-Met-Lys.

Preferably, when either $X_n$ or $X_m$ is an amino acid residue sequence, $X_n$ or $X_m$ contains up to about 20 residues, more preferably, up to about 10 residues, and most preferably, up to about 5 amino acid residues. Typically, $X_n$ and $X_m$ each have an amino acid residue sequence identical to the corresponding sequence found in human fibrinogen.

In a still further preferred embodiment, a polypeptide of the invention has the formula:

H—Y—OH where Y is as defined previously.

A polypeptide of the present invention can be used to generate a variety of useful antibodies by means described herein. The utilities of the polypeptides will be apparent from the discussion provided hereinbelow.

Typically an instant polypeptide is not glycosylated, i.e., it is synthesized either directly by standard peptide synthesis techniques or by procaryotic host expression of a recombinant DNA molecule of the present invention. A eucaryotically produced polypeptide of the present invention is typically glycosylated.

An instant polypeptide can incorporate a variety of changes, such as insertions, deletions, and substitutions of amino acid residues which are either conservative or nonconservative as long as the resulting polypeptide molecule exhibits the desired properties. The "desired properties" as referred to herein include that the polypeptide is immunogenic in a suitable host and able to generate antibodies to the polypeptide, and preferably to a GPIIb-IIIa-fibrinogen complex, e.g., as expressed on platelets. Additionally, the polypeptide is antigenic so that an antibody is immunoreactive with the polypeptide, and preferably with a GPIIb-IIIa-fibrinogen complex.

When an instant polypeptide incorporates conservative substitutions of the sequences corresponding to those depicted above, the substituted amino acid residues are replaced by another, biologically similar amino acid residue such that the resulting polypeptide has an amino acid residue sequence that is different from (other than) a sequence of fibrinogen. Some examples of conservative substitutions include substitution of a hydrophobic residue such as isoleucine, valine, leucine or methionine for another hydrophobic residue. Also, a polar residue such as arginine, glycine, glutamic acid, aspartic acid, glutamine, asparagine, and the like, can be conservatively substituted for another member of this group. Still another aspect of a polypeptide incorporating conservative substitutions occurs when a substituted amino acid residue replaces an unsubstituted parent amino acid residue. Examples of substituted amino acids may be found at 37 C.F.R. §1,822(b)(4), which species are incorporated herein by reference. When the polypeptide has an amino acid residue sequence that corresponds to the sequence of fibrinogen but has one or more conservative substitutions, preferably no more than about 20%, and more preferably no more than about 10%, of the amino acid residues of the native protein are substituted. Particularly preferred conservatively substituted polypeptides are monosubstituted analogs of a human gamma chain amino acid residue sequence, such as those identified above.

A polypeptide of the present invention can be synthesized by any of the peptide synthetic techniques known to those skilled in the art. A summary of some of the techniques available can be found in J. M. Stuard and J. D. Young, "Solid Phase Peptide Synthesis", W. H. Freeman, Co., San Francisco (1969), J. Meinhofer, "Hormonal Proteins and Peptides" Vol. 2, pp. 46, Academic Press (New York) 1983, and U.S. Pat. No. 4,631,211, which description is incorporated herein by reference. When a polypeptide desired for use in the present invention is relatively short (less than about 40 amino acid residues in length) direct peptide synthetic techniques are generally favored, usually by employing a solid phase technique such as that of Merrifield [Merrifield JACS, 85:2149 (1963)].

A further aspect of the invention is for a polypeptide composition comprising a polypeptide of the present invention admixed with a suitable pharmaceutical excipient, preferably in unit dosage form. The polypeptide composition can be used to "neutralize" antibody molecules that immunoreact with a polypeptide of the invention. Thus, antibody molecules present in a mammal which immunoreact with an instant polypeptide molecule can be effectively removed from circulation in the mammal due to complexation of peptide and antibody.

A preferred aspect of the invention is when the antibody recognizes a polypeptide in the polypeptide composition which defines a RIBS epitope on human fibrinogen immunocomplexed with human GPIIb-IIIa, as expressed on platelets. A particularly preferred embodiment employs a 2G5 MAb neutralized by a polypeptide that includes a before listed amino acid residue sequence, or a conservatively substituted sequence thereof.

In all other aspect of the invention, an instant polypeptide can be used to generate antibodies immunoreactive with the polypeptide by the methods described herein. The polypeptide can be used to immunize an animal either alone or in conjugation with another chemical group, e.g., a carrier molecule. Any carrier group tolerated by the host is contemplated.

C. Monoclonal Antibodies

A monoclonal antibody (MAb) of the present invention is characterized as comprising antibody molecules that immunoreact with a ligand's receptor-induced binding site. A MAb of the present invention immunoreacts with a RIBS, but does not substantially immunoreact with either the unbound (free) ligand or receptor, i.e., when either the ligand or receptor is free in solution, thereby permitting distinguishing between the receptor-bound and un-bound forms of a ligand. A MAb of the present invention does not "substantially;" immunoreact with another species as described herein when the monoclonal antibody immunoreaction with a ligand-receptor complex is inhibited by no more than about 15 percent, and preferably less, as by competitive binding with free ligand or unbound receptor.

In one preferred embodiment, a subject MAb comprises antibody molecules that immunoreact with a RIBS expressed by a cytoadhesin-ligand complex. Cytoadhesin is a name given to a superfamily of receptor molecules all of which bind to a ligand that contains the amino acid residue sequence arginine-glycine-aspartic acid or RGD. [Plow et al., *Proc. Natl. Acad. Sci. USA,* 83:6002 (1986)]. This superfamily has also been given the name Integrin. [Ruoslahti et al., *Science,* 238:491–497 (1987)]. The particular cytoadhesin of exemplary interest herein is GPIIb-IIIa, also known as a platelet fibrinogen receptor.

A preferred monoclonal antibody of this invention is secreted (produced) by one of the following hybridomas: hybridoma 2G5 having ATCC designation HB9847, hybridoma 2F10 having ATCC designation HB9844, hybridoma 3G11 having ATCC designation HB9845, and hybridoma 4G10 having ATCC designation HB9846. The above hybridomas were deposited at the American Type Culture Collection, 12301 Parklawn Drive, Rockville, Md., 20852, USA on Sep. 29, 1988 pursuant to the Budapest Treaty.

D. Methods for Producing Monoclonal Antibody Compositions

The present invention contemplates a method of forming a monoclonal antibody that immunoreacts with a receptor-induced binding site. The method comprises the steps of:

(a) Immunizing an animal with a receptor-ligand complex. This is typically accomplished by administering an immunologically effective amount, i.e., an amount sufficient to produce an immune response, of immunogen to an immunologically competent mammal. Preferably, the mammal is a rodent such as a rabbit, rat or mouse, although other mammals such as goats, horses, and simians can be used. The mammal is then maintained for a time period sufficient for the mammal to produce cells secreting antibody molecules that immunoreact with the receptor-ligand complex.

(b) A suspension of antibody-secreting cells removed from the immunized mammal is then prepared. This is typically accomplished by removing the spleen of the mammal and mechanically separating the individual spleen cells in a physiologically tolerable medium using methods well known in the art.

(c) The suspended antibody producing cells are treated with a transforming agent capable of producing a transformed ("immortalized") cell line. Transforming agents and their use to produce immortalized cell lines are well known in the art and include DNA viruses such as Epstein Barr virus (EBV), simian virus 40 (SV40), polyoma virus and the like, RNA viruses such as Moloney murine leukemia virus (Mo-MuLV), Rous sarcoma virus and the like, myeloma cells such as P3X63-Ag8.653, Sp2/O-Ag14 and the like.

In preferred embodiments, treatment with the transforming agent results in the production of a hybridoma by fusing the suspended spleen cells with mouse myeloma cells from a suitable cell line by the use of a suitable fusion promoter. The preferred ratio is about 5 spleen cells per myeloma cell in a suspension containing about $10^8$ splenocytes. A preferred fusion promoter is polyethylene glycol having an average molecule weight from about 1000 to about 4000 (commercially available as PEG 1000); however, other fusion promoters known in the art may be employed.

The cell line used should preferably be of the so-called "drug resistant" type, so that unfused myeloma cells do not survive in a selective medium, while hybrids will survive. The most common class is 8-azaguanine-resistant cell lines, which lack the enzyme hypoxanthine guanine phosphoribosyl transferase and hence are not supported by HAT (hypoxanthine, aminopterin, and thymidine) medium. It is also generally preferred that the myeloma cell line used be of the so-called "non-secreting" type, in that it does not itself produce any antibody, although secreting types may be used. In certain cases, however, secreting myeloma lines may be preferred.

(d) The transformed cells are then cloned, preferably to monoclonality. The cloning is preferably performed in a tissue culture medium that will not support non-transformed cells. When the transformed cells are hybridomas, this is typically performed by diluting and culturing in separate containers, the mixture of unfused spleen cells, unfused myeloma cells, and fused cells (hybridomas) in a selective medium that does not support the unfused myeloma cells for a time sufficient to permit death of the unfused cells (about one week). The dilution and culturing is carried out in separate containers, and the dilution may be a limiting dilution in which the volume of diluent is statistically calculated to isolate a certain number of cells (e.g., 1-4) in each separate container (e.g., each well of a microliter plate). The medium is one (e.g., HAT medium) that does not support the drug-resistant (e.g., 8-azaguanine-resistant) unfused myeloma cell line.

(e) The tissue culture medium of the cloned transformants is evaluated for the presence of secreted antibody molecules that do not immunoreact with a free ligand but do immunoreact with the ligand when it is present as part of a receptor-ligand complex. The evaluation is performed using well known immunological techniques, as is described hereinafter.

(f) Once a desired transformant has been identified in step (e), it is selected and grown in a suitable tissue culture medium for a suitable length of time, followed by recovery of the desired antibody from the culture supernatant. A suitable medium and length of culturing time are also well known in the art or are readily determined.

To produce a much greater concentration of slightly less pure monoclonal antibody, the desired hybridoma can be injected into mice or other mammals in which the hybridoma can grow, preferably syngeneic or semi-syngenic mice. The hybridoma causes formation of antibody-producing tumors after a suitable incubation time, which results in a high concentration of the desired antibody (about 5-20 mg/ml) in the bloodstream and peritoneal exudate (ascites) of the host mouse.

Media and animals useful for the preparation of these compositions are both well known in the art and commercially available, and include synthetic culture media, inbred mice and the like. An exemplary synthetic medium is Dulbecco's minimal essential medium [DMEM; Dulbecco et al., *Virol.* 8:396 (1959)] supplemented with 4.5 gm/l glucose, 20 mm glutamine, and 20% fetal calf serum. An exemplary inbred mouse strain is the Balb/c.

A monoclonal antibody produced by the above method can be used, for example, in diagnostic and therapeutic modalities, discussed in greater detail hereinafter wherein formation of a RIBS-containing immunoreaction product is desired. Such uses include, for example, the diagnostic methods and systems of the present invention to detect fibrinogen-bound platelets in a body sample, e.g., for in vivo detection of a thrombus, dispersing a thrombus, or thrombus imaging.

A RIBS monoclonal antibody is typically utilized in an aqueous composition. That composition can be the tissue culture medium or ascites fluid as obtained or in diluted form. Such compositions are typically utilized in vitro.

For in vivo uses, the RIBS monoclonal antibody is typically purified as by precipitation in ammonium sulfate, affinity purification procedure and the like and then utilized in an aqueous composition of a pharmaceutically acceptable diluent. The concentration of RIBS monoclonal antibodies in that aqueous composition is adjusted to suit the desired use.

E. Therapeutic Methods and Compositions

Monoclonal antibodies secreted by any of the before-described deposited hybridomas, and antibodies having similar immunospecificity, are particularly useful in areas relating to blood clots or thrombi. This is because those types of anti-RIBS monoclonal antibodies immunoreact with the fibrinogen-GPIIb-IIIa receptor complex that is present on activated platelets containing bound fibrinogen, and platelet-bound fibrinogen is involved in thrombus formation. Furthermore, since by definition, those RIBS monoclonal antibodies do not immunoreact with soluble fibrinogen as is present in vivo in circulating blood, extreme specificity of immunoreaction can be had by use of one or more of those monoclonal antibodies. Descriptions of some preferred uses of an instant antibody composition follow.

1. Thrombus Dispersement

One aspect of this invention is for a method for the dispersement of a thrombus. Here, the antibody molecules of a monoclonal antibody produced by at least one of the ATCC deposited hybridomas 2G5, 2F10, 3G11, and 4G10 is chemically linked to a plasminogen-activating enzyme to form a conjugate in which the binding of the antibody portion of the conjugate to its RIBS is substantially unimpaired and the plasminogen activating activity of the enzyme is substantially unimpaired. Methods of preparing an antibody-protein conjugate in which the activities of both portions of the conjugate are substantially unimpaired are well known by skilled workers.

A plasminogen-activating enzyme refers to the group of fibrinolytic drugs in the class of prothrombolysis, such as tissue plasminogen activators that induce thrombolysis without systemic fibrinolysis or fibrinogen break down. Other fibrinolytic drugs contemplated are those which interact with the proactivator plasminogen and include, but are not limited to streptokinase, urokinase (u-PA), and tissue plasminogen activator (t-PA).

In accordance with this method, a pharmaceutically acceptable aqueous composition containing a thrombus-dispersing amount of a before-described conjugate is administered, such as by intravenous injection or infusion, to a mammal such as a human having a thrombus to be dispersed. The mammal so treated is maintained for a time period sufficient for the antibody portion of the conjugate to immunoreact with the platelet-bound fibrinogen complex present in the thrombus and for the plasminogen-activating enzyme portion of the conjugate to activate plasminogen. Since removal of the conjugate would be a difficult and time-consuming task, the treated mammal is maintained for a time sufficient for its own body to clear the conjugate by usual means.

2. Inhibition of Thrombus Formation

Another treatment method is contemplated for animal subjects at risk of thrombus formation, such as persons in the first several days after a major operation, e.g., a coronary by-pass operation.

Here; a thrombus-inhibiting amount of a monoclonal antibody, containing antibody molecules produced by at least one of the ATCC deposited hybridomas 2G5, 2F10, 3G11 and 4G10, present in a pharmaceutically acceptable aqueous composition is administered to a mammal such as a human in whom thrombus formation is to be inhibited. The treated mammal (administered mammal) is maintained for a time period sufficient for the administered RIBS monoclonal antibodies to be cleared from its body by usual means.

In this method, the immunoreaction of the RIBS monoclonal antibodies with activated platelets containing bound fibrinogen inhibits thrombus formation. Of course, since a RIBS monoclonal antibody immunoreacts with the fibrinogen-GPIIb-IIIa complex on the platelet and not with fibrinogen in the blood, normal function of the treated animal is not impaired.

In a related embodiment a method of inhibiting platelet aggregation is contemplated that comprises administering to a platelet containing solution a pharmaceutically acceptable aqueous composition containing monoclonal antibody molecules produced by at least one of the ATCC deposited hybridomas 2G5, 2F10, 3G11 and 4G10. A platelet aggregation-inhibiting amount of the antibody is administered in vivo to a animal subject in which inhibition of platelet aggregation is desired, or is admixed in vitro with a platelet-containing solution, such as plasma or blood. The immunoreaction of the RIBS monoclonal antibodies with fibrinogen-GPIIb-IIIa complex on the platelets forms an immunoreaction product that inhibits platelet aggregation.

A single, before-described, RIBS monoclonal antibody can be used in each of the above methods, or a mixture containing more than one can be utilized. Thus, although each of the monoclonal antibodies produced by the four ATCC deposited hybridomas shares the property of being a RIBS monoclonal, each antibody combining site does not immunoreact with the same epitope. Thus, advantage is obtained by using a mixture of those monoclonal antibodies (alone or in the conjugate) so that multiple binding of the combining sites to a single bound fibrinogen molecule can occur.

It is to be understood that although the two above methods have been described in terms of the RIBS monoclonal antibodies that immunoreact specifically with the fibrinogen-GPIIb-IIIa complex, similar methods are applicable for other ligand-receptor complexes that contain RIBS.

The preparation of a pharmaceutically acceptable aqueous composition that contains antibody molecules as active ingredients is well understood in the art. Typically, such compositions are prepared as injectables, either as liquid solutions or suspensions, however, solid forms suitable for solution in, or suspension in, an aqueous liquid prior to injection can also be prepared. The preparation can also be emulsified.

The conjugate or monoclonal antibody alone is often mixed with an excipient that is pharmaceutically acceptable and compatible with the conjugate or monoclonal antibody, as is well known. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A conjugate or monoclonal antibody can be formulated into the above aqueous composition as neutralized pharmaceutically acceptable salt forms. Pharmaceutically acceptable salts include the acid addition salts (formed with the free amino groups of the enzyme or antibody molecule) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylaminoethanol, histidine, procaine, and the like.

The therapeutic antibody molecule-containing compositions are conventionally administered intravenously, as by injection of a unit dose, for example. A composition is administered in a manner compatible with the dosage formulation and in a therapeutically effective, i.e., in a thrombus-dispersing or thrombus-inhibiting, amount.

3. Antibody Neutralization

Therapeutic methods are also contemplated for "neutralizing" or inhibiting an anti-RIBS antibody which immunoreacts with a polypeptide of this invention. Hence, the concentration of an antibody present in a patient at an unacceptably high level, as when the antibody inhibits platelet aggregation excessively, can be effectively reduced by administering to the patient a therapeutically effective amount of a before-described polypeptide. Typically, the polypeptide is administered as a sterile pharmaceutical composition and in a unit dosage form as described herein.

4. Administration Regimes

"Unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Unit dosage forms are typically prepared from the frozen or dried antibody by dispersement in a physiologically tolerable (acceptable) diluent or vehicle such as water, saline or phosphate-buffered saline to form an aqueous composition. Such diluents are well known in the art and are discussed, for example, in *Remington's Pharmaceutical Sciences*, 16th Ed., Mack Publishing Company, Easton, PA (1980) at pages 1465–1467.

Dosage forms can also include an adjuvant as part of the diluent. Adjuvants such as complete Freund's adjuvant (CFA), incomplete Freund's adjuvant (IFA) and alum are materials well known in the art, and are available commercially from several sources.

The quantity of antibody composition to be administered depends, inter alia, on the animal species to be treated, the subject animal's size, the size of the thrombus (if known), the amount of fibrinogen-bound platelets present, and the capacity of the subject to utilize the conjugate or monoclonal antibody. Precise amounts of conjugate or monoclonal antibody required to be administered depend on the judgment of the practitioner and are peculiar to each individual, particularly where humans are the treated animals. Dosage ranges, however, can be characterized by a therapeutically effective blood concentration and can range from a concentration of antibody-containing conjugate, or antibody alone, of the present invention from about 0.01 uM to about 100 uM, preferably about 0.1 uM to 10uM.

Suitable regimes for initial administration and booster injections are also variable, but are typified by an initial administration followed by repeated doses at one or more hour intervals by a subsequent injection or other administration. Alternatively, continuous intravenous infusion sufficient to maintain therapeutically effective concentrations in the blood are contemplated.

F. Diagnostic Systems

A diagnostic system in kit form of the present invention includes, in an amount sufficient for at least one assay, a RIBS monoclonal antibody of the present invention, such as one produced by one of the four ATCC deposited hybridomas, as a separately packaged reagent. A label for indicating the presence of an immunoreaction between the RIBS and RIBS monoclonal antibody is also preferably included in the same or a separate package. Instructions for use of the packaged reagent are also typically included.

Instructions for use typically include a tangible expression describing the reagent concentration or at least one assay method parameter such as the relative amounts of reagent and sample to be admixed, maintenance time periods for reagent/sample admixtures, temperature, buffer conditions and the like.

One embodiment of this invention is a diagnostic system in kit form for assaying for fibrinogen-bound platelets in a platelet-containing vascular fluid sample, such as blood or plasma. The system comprises a package containing a monoclonal antibody that immunoreacts with a RIBS expressed by the receptor-ligand complex. Preferably, the anti-RIBS antibody molecules of the monoclonal antibody are those produced by one of the following hybridomas: hybridoma 2G5, hybridoma 2F10, hybridoma 3G11, and hybridoma 4G10. Preferably, the antibody molecules are present as a monoclonal antibody composition which contains more than one particular monoclonal antibody. Further preferred are kits wherein the antibody molecules are linked to a radionuclide label, preferably a $^{125}I$-label. Useful labels are discussed hereinafter.

In another embodiment, a diagnostic system of the present invention is suitable for assaying for the presence of a thrombus in vivo. The system comprises a package containing monoclonal antibody molecules that immunoreact with a RIBS expressed by a receptor-ligand complex. Preferably, the antibody molecules present are those secreted by a hybridoma selected from the group consisting of 2G5, 2F10, 3G11, and 4G10. The antibody molecules are preferably linked to an in vivo label or indicating means.

Although a kit for in vivo imaging can often be utilized for in vitro assays, it is understood that the converse need not be true. For example, the monoclonal antibodies utilized for in vivo work should be free of pyrogens as should any buffer salts of aqueous compositions and reagents. Freedom from pyrogen content is not a necessity for in vitro assays. Additionally, the indicating means useful for in vivo imaging is typically different from that used in vitro, as is discussed hereinafter. Thus, the assay system is suitable for in vivo imaging, and suitable buffer salts, aqueous solutions and indicating means can be supplied as part of the kit in the same or separate packages.

In preferred embodiments, a diagnostic system of the present invention further includes a label or indicating means capable of signaling the formation of an innnunoreaction complex containing an antibody molecule of the present invention.

As used herein, the terms label and indicating means in their various grammatical forms refer to single atoms and molecules that are either directly or indirectly involved in the production of a detectable signal to indicate the presence of a complex. In vivo labels or indicating means are those useful within the body of a human subject and include $^{111}$In, $^{99}$Tc, $^{67}$Ga, $^{186}$Re, and $^{132}$I.

Any label or indicating means can be linked to or incorporated in an antibody molecule that is part of a conjugate or monoclonal antibody composition of the present invention, and those atoms or molecules can be used alone or in conjunction with additional reagents. Such labels are themselves well known in clinical diagnostic chemistry and constitute a part of this invention only insofar as they are utilized with otherwise novel protein methods and/or systems.

The linking of labels, i.e., labeling of, to antibodies is well known in the art. For instance, antibody molecules produced by a hybridoma can be labeled by metabolic incorporation of radioisotope-containing amino acids provided as a component in the culture medium. See, for example, Galfre et al., *Meth. Enzymol*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The in vitro diagnostic systems can also include, preferably as a separate package, a specific binding agent. A "specific binding agent" is a molecular entity capable of selectively binding a monoclonal antibody of the present invention but is not itself an antibody molecule of the present invention. Exemplary specific binding agents are second antibody molecules, complement proteins or fragments thereof, *S. aureus* protein A and the like. The specific binding agent binds the RIBS monoclonal antibody molecule of this invention when that monoclonal antibody is present as part of an immunocomplex with the ligand-receptor complex. In preferred embodiments, the specific binding agent is labeled. However, when the diagnostic system includes a specific binding agent that is not labeled, the specific binding agent is typically used as an amplifying means or reagent and a second reagent that is labeled binds to the specific binding agent (amplifying means). In these embodiments, the labeled second reagent is capable of specifically binding the amplifying means when the amplifying means is bound to a RIBS monoclonal antibody-containing immunocomplex.

A diagnostic kit of the present invention can be used in an "ELISA" format to detect the presence or quantity of ligand-receptor complex such as fibrinogen-bound platelets in a body fluid sample such as serum, plasma or urine. "ELISA" refers to an enzyme-linked immunosorbent assay that employs an antibody or antigen bound (here, the RIBS-containing ligand-receptor complex) to a solid phase matrix that forms a solid support and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are all incorporated herein by reference.

In a preferred ELISA kit embodiment, an antibody molecule of the present invention is affixed to a solid matrix to form a solid support that is separately packaged in the subject diagnostic systems. The antibodies are typically affixed to the solid matrix by adsorption from an aqueous medium although other modes of affixation, well known to those skilled in the art can be used.

A labeled specific binding agent that binds to a ligand-receptor complex or to one of its constituents, or an unlabeled specific binding agent plus a labeled second reagent that binds to the specific binding agent, is also included in one or two separate packages, respectively, in the kit. Using one of the monoclonal antibodies produced by one of the ATCC deposited hybridomas as exemplary of a matrix-bound antibody, labeled anti-fibrinogen antibodies, as are commercially available, are exemplary of the specific binding agent.

Useful solid matrices are well known in the art. Such materials include the cross-linked dextran available under the trademark SEPHADEX from Pharmacia Fine Chemicals (Piscataway, N.J.); agarose; polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microliter plate such as those made from polystyrene or polyvinylchloride.

A monoclonal antibody (labeled or unlabeled), labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a kit system. A solid support matrix such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

G. Assay Methods

The present invention contemplates a method for detecting a receptor-ligand complex, as, for example, is found in a thrombus or in fibrinogen-bound platelets, preferably, GPIIb-IIIa:fibrinogen. The method utilizes the expression of a receptor-induced binding site (RIBS) and a monoclonal antibody molecule that immunoreacts with the RIBS in the ligand portion of the receptor-ligand complex, but does not react with a non-bound receptor or a non-bound ligand. Those skilled in the art will understand that there are numerous well known clinical diagnostic chemistry procedures that can be utilized to form such immunocomplexes. Thus, while exemplary assay methods are described herein, the invention is not so limited.

1. Thrombus Detection

More specifically, a method for detecting the presence of a thrombus in a mammal such as a human is contemplated. An aqueous composition containing an imaging-effective amount of a monoclonal antibody of the present invention containing antibody molecules linked to an in vivo indicating means is intravenously administered to a mammal such as a human in need of such treatment.

The administered mammal is maintained for a predetermined time period sufficient for the labeled antibody molecule to immunoreact with the platelet-bound fibrinogen complex present as part of a thrombus. The subject mammal is then assayed for the presence and preferably location of any labeled immunocomplex formed, and thereby detecting, and preferably locating, the thrombus. When a labeled RIBS monoclonal antibody normally contains a radionuclide as the label or indicating means, the imaging assay is carried out by usual, well known radioimaging techniques. Such techniques can distinguish the relatively high concentration of radiolabel at the thrombus from the relatively lower systemic amount of radiolabel. Where relatively long-lived radioisotopes are utilized, the administered mammal can be maintained for a time period sufficient for substantial systemic clearance of the labeled monoclonal antibody to thereby provide a relatively still lower amount of background signal from the radiolabel.

2. Detection of Fibrinogen-Bound Platelets in a Body Sample

Various heterogeneous and homogeneous assay protocols can be employed, either competitive or non-competitive, for detecting the presence and preferably amount of fibrinogen-bound platelets in a platelet-containing and/or free fibrinogen-containing body sample, preferably a body fluid sample such as blood or a platelet-containing portion of blood. For example, a heparin-preserved (non-clotted) blood sample and an $^{125}I$-labeled form of one of the before-discussed, deposited RIBS antibody molecules are admixed. Amounts and concentrations of blood sample and labeled monoclonal antibody are, of course, utilized so that a meaningful result can be obtained. The immunoreaction admixture thus formed is maintained under biological assay conditions for a time period sufficient for fibrinogen-bound platelets present in the sample to immunoreact with the labeled antibodies and form a labeled immunoreaction product. The labeled immunoreaction product, when present, is then separated from any non-reacted labeled-antibodies that may be present. In homogenous assays, separation is typically by centrifugation sufficient to pelletize all platelets present in the sample. In heterogeneous assays such as an ELISA, the immunoreaction product is bound to the solid support and the separation is typically effected by a washing step in which any unbound RIBS antibody is discarded and the solid support-bound imunoreaction product is retained.

It should be understood that where an unlabeled RIBS monoclonal antibody is used to immunoreact with a RIBS-containing ligand-receptor complex, a second admixture is formed between the before-described, separated immunocomplex and a labeled binding reagent or unlabeled binding reagent used as an amplifying means. That reaction mixture is maintained under biological conditions for a time period sufficient for a second binding complex to form between the first-formed immunocomplex and the specific binding reagent.

Where the specific binding reagent comprises antibody molecules, that second binding complex is a second immunocomplex. Where S. aureus protein A is used, for example, the second binding complex does not rely for binding upon the antibody binding site, and that complex is best referred to as a binding complex. Since an immunocomplex is a specific binding complex, the complex formed between the specific binding reagent and first-named immunocomplex is a second binding complex. The second binding complex is thereafter separated from any unreacted specific binding reagent that may be present, as by a previously mentioned technique, and the presence of the label and thereby immunocomplex is determined, and preferably quantified.

Where the specific binding reagent is not labeled and is used as an amplifying means, a third admixture is formed from the above, separated second binding complex, when present, and a label-containing second binding reagent. The presence of the label in the second binding complex is, of course, not determined in the above-described method where no labeled reagent was admixed. The before-described maintenance and separation steps are repeated for this aspect of the method with a label-containing third binding complex being formed and retained. The presence and preferably the amount of the label is thereafter determined.

Thus, in each of the above-described aspects of this assay, the presence and preferably the amount of the label provides the basis for determining the presence and preferably the amount of fibrinogen-bound platelets.

It is; noted that the worker carrying out an above-described assay usually will not know whether one or more of the immunocomplex or binding complexes has indeed formed until the amount of label present is determined. Nevertheless, all of the steps of a given assay procedure are carried out as if the RIBS-containing complex is indeed present.

It is to be emphasized that because of the unique specificity of the RIBS monoclonal antibodies, the above-described assay for fibrinogen-bound platelets and the before-described imaging assay for a thrombus can be and preferably are carried out in the presence of both free platelets and free fibrinogen, i.e., non-complexed platelets and fibrinogen. As a result, special handling procedures such as separations and washing steps need not be carried out on the body sample prior to use of that sample in an assay. This feature is common to all assays using RIBS monoclonal antibodies.

3. Antibody Detection

A method for detecting an instant antibody, as in a blood sample, is also contemplated. Such a method comprises the steps of:

(a) subjecting an aqueous solution suspected of containing the antibody to a polypeptide of this invention immobilized on a surface, e.g., a Sepharose column;

(b) maintaining the antibody in contact with the immobilized polypeptide for a sufficient time and under predetermined reaction conditions so that an antibody-polypeptide immunocomplex is formed; and (c) determining the presence of immunocomplex formed which is related to the presence of antibody in the solution tested. Detection can be by radiolabelling of the antibody, ELISA analysis of bound antibody, and the like, as is well known.

Biological assay conditions are those that maintain the biological activity of the antibody molecules of this invention and the fibrinogen-bound platelets or other RIBS-containing complex to be assayed. Those conditions include a temperature range of about 4° C. to about 45° C., preferably about 37° C., a pH value range of about 5 to about 9, preferably about 7 and an ionic strength varying from that of distilled water to that of about one molar sodium chloride, preferably about that of physiological saline. Methods for optimizing such conditions are well known in the art.

EXAMPLES

The following examples illustrate but do not limit the scope of the present invention.

1. Hybridoma and Monoclonal Antibody Production

Monoclonal antibodies were produced using standard hybridoma technology. Briefly, Balb/c mice were immunized and subsequently boosted three times with about 50 micrograms (ug) per mouse of fibrin D-dimer immunogen prepared substantially as described in Cierniewski et al., Thromb. Haemostas., 48:33–37 (1982).

Subsequently, $1.23 \times 10^8$ splenocyte cells from one immunized mouse whose antibodies immunoreacted with the immunogen were admixed with $2.46 \times 10^7$ P3Ag8653.1 mouse myeloma cells in the presence of the cell fusion promoter polyethylene glycol 4000. The antibody producing cells thus transformed were transferred to 96-well microtiter plates at a density of about $3 \times 10^4$ cells per well and cultured.

Tissue culture supernatants from 235 wells appearing to contain viable hybridomas after about 14 days of culturing were screened by radioimmune assay for the presence of anti-RIBS antibody molecules. Briefly, 100 microliters (ul) of phosphate-buffered saline (PBS) containing either 1 ug/ml of fibrinogen or low density lipoprotein (LDL) (control) were admixed into the wells of flat-bottom 96-well polyvinyl microtiter plates as solid phase matrix. The plates were then maintained for about 16–20 hours at 4° C. to permit the fibrinogen or LDL to adsorb onto the surface of the wells to form a solid support. The coating solution was removed by shaking, the wells were rinsed, and 100 ul of blocking solution (PBS containing 5% normal goat serum) were admixed into each well to block excess protein binding sites.

The wells were maintained for about 30 minutes at 37° C. and then the blocking solution was removed. Into each well were then admixed 100 ul of either (a) hybridoma tissue culture supernatant diluted 1:10 in PBS, or (b) hybridoma supernatant diluted 1:10 in PBS containing 100 ug/ml fibrinogen as a competitive inhibitor. The immunoreactions admixtures thus formed were maintained at room temperature for about 16–20 hours at 4° C. to permit the formation of a solid phase-bound immunoreaction product and a liquid phase, including any non-bound monoclonal antibody molecules.

To each well were then admixed 100 ul of $^{125}$I-labeled goat anti-mouse IgG. The labeling immunoreaction admixture thus formed was maintained about 6–20 hours at 4° C. to permit formation of a $^{125}$I-labeled second solid-phase immunoreaction product. The solid and liquid phases were separated to remove any non-bound $^{125}$I-goat anti-mouse IgG. The amount of $^{125}$I-bound to each well was determined by gamma scintillation.

The presence of at least about 3 times the amount of non-specifically bound $^{125}$I, as determined from the LDL-coated wells in a fibrinogen-coated well, indicated the presence of anti-fibrinogen antibodies in a tissue culture supernatant. A reduction of solid-phase bound $^{125}$I by no more than about 15% by the presence of liquid-phase fibrinogen competitor in the immunoreaction admixture [part (b) above] indicated the presence of an anti-RIBS antibodies in the tissue culture supernatant.

The above screening procedure resulted in the identification of 4 hybridomas, designated 2G5, 2F10, 3G11 and 4G10, that produce anti-RIBS antibodies that bind a fibrinogen:GPIIb-IIIa complex. The hybridomas have the following ATCC deposit designations: 2G5(HB9847), 2F10(HB9844), 3G11(HB9845), and 4G10(HB9846).

Each of the four above described hybridomas was cloned twice by limiting dilution and subsequently used to produce ascites fluid. The antibodies were then isolated from the ascites fluids by using protein A Sepharose.

Compositions containing Fab fragments of the monoclonal antibody (Mab) 2F10 were prepared by digestion of protein A Sepharose-isolated MAb 2F10 with papain (200:1 weight per weight of MAb to papain) for 6 hours at 37° C. following the methods of Mage et al., Methods in Enzymology, 70: 142–50 (1980). Undigested antibody and Fc fragments were removed from the Fab fragments by chromatography on protein A Sepharose. The resulting Fab fragments were collected from the Sepharose to form a 2F10 Fab preparation.

2. Detection of a Fibrinogen:GPIIb-IIIa RIBS on Activated Platelets

Monocolonal antibodies produced by hybridomas 2G5, 2F10 and 3G11, i.e. MAb 2G5, MAb 2F10 and MAb 3G11, respectively, were examined for their ability to immunoreact with a cell surface bound RIBS. Each of the four monoclonals was $^{125}$I labeled using standard Chloramine-T methodology. Greenwood et al., Bio. Chem. J., 89:114–123 (1963).

Sixty milliliters (ml) of whole human blood was collected in 5 ml of ACD (0.065M citric acid, 0.085M sodium citrate, 2% dextrose) containing hirudin (Sigma Chemical Co., St. Louis, Mo.) at a formula concentration of 0.06 units per ml (U/ml) and centrifuged for 15 minutes at $120 \times g$. The resulting supernatant, designated platelet rich plasma, was recovered, isolated and further centrifuged for 15 minutes at $1200 \times g$ to form a pellet of isolated platelets.

The isolated platelets were resuspended in 2 ml of calcium-free Tyrodes buffer (0.13M NaCl, 0.0026M KCl, 0.002M $MgCl_2$-$6H_2O$, 5 mM Hepes, 0.012M $NaHCO_3$, pH 7.2) containing 1 mg/ml bovine serum albumin (BSA) and 1 mg/ml dextrose. The platelet suspension was then applied to a Sepharose CL2B column (40 ml total bed volume; Pharmacia Inc., Piscataway, N.J.) equilibrated with the same Tyrodes' buffer. Washed platelets were recovered from the void volume of the CL2B column in a final volume of about 4 to 5 ml.

Samples of the washed platelets were then stimulated (activated) by admixture with either adenosine diphosphite (ADP) to a concentration of 10 micromolar (uM), or thrombin to a concentration of 0.1 units/ml. Some samples of ADP-stimulated platelets were also admixed with fibrinogen to a fibrinogen concentration of 1 mM.

To each sample of platelets, including some non-simulated control samples, was admixed a $^{125}$I-labeled MAb to a concentration of 10 nanomolar (nM). The immunoreaction admixture thus formed was maintained for 30 minutes at 22° C. to permit immunoreaction product formation. The immunoreaction products were separated from non-bound $^{125}$I-MAb by centrifugation through 0.3 ml of 20% sucrose. The amount of $^{125}$I-MAb associated with the platelet pellet was determined by scintillation spectrometry.

The results of this study, shown in Table 2 below, indicate that the anti-RIBS monoclonal antibodies do not substantially immunoreact with non-stimulated platelets. However, when the platelets are stimulated with an agonist such as ADP or thrombin, a significant immunoreaction of the MAbs with the fibrinogen:GPIIb-IIIa complex on the cells is obtained. Stimulation of the platelets with ADP or thrombin results in secretion and surface binding by GPIIb-IIIa of the platelet-endogenous fibrinogen. Addition of exogenous fibrinogen did not neutralize (inhibit) the binding of $^{125}$I-MAb to the stimulated platelets, thus indicating the MAbs are RIBS-specific, i.e., they do not immunoreact with free fibrinogen in solution. Similar results were obtained with MAb 4G10.

TABLE 2

| Platelets | $^{125}$I-MAb Bound (cpm/platelet) | | |
|---|---|---|---|
| | 2G5 | 2F10 | 3G11 |
| Nonstimulated | 1,200 | 2,800 | 1,300 |
| ADP-stimulated | 33,750 | 43,600 | 31,550 |
| ADP-stimulated + fibrinogen | 35,600 | 51,300 | 30,150 |
| Thrombin-stimulated | 28,620 | 32,000 | 28,400 |

To emphasize the point that exogenously added fibrinogen is not cell-associated (i.e., is not part of cell receptor-ligand complex) but yet does not neutralize the immunoreactivity of MAbs 2G5, 2F10, 3G11 and 4G10 with the fibrinogen:GPIIb-IIIa complex, the immunoreactivity of the MAbs with the platelets was examined using platelet rich plasma containing 2-3 mg/ml fibrinogen.

As shown in Table 3 below, despite the vast excess of free fibrinogen, each of the four $^{125}$I-MAbs immunoreacted with fibrinogen:GPIIb-IIIa RIBs on the platelet surface.

TABLE 3

| Platelets | $^{125}$I-MAb Bound (cpm/platelet) | | | |
|---|---|---|---|---|
| | 2G5 | 2F10 | 3G11 | 4G10 |
| Nonstimulated | 174 | 662 | 218 | 678 |
| ADP-stimulated | 17,823 | 7,471 | 20,382 | 19,540 |

As a further indication of specificity of the four deposited MAbs for RIBS, similar MAb binding studies were conducted using cells containing a Mac-1 receptor rather than platelets having the GPIIb-IIIa platelet glycoprotein receptor. Both Mac-1 and GPIIb-IIIa bind specifically to fibrinogen in a receptor-ligand fashion, but the two interactions produce distinct biological results. In the binding studies, the four deposited RIBS do not exhibit immunoreaction with fibrinogen-Mac-1 complex, but do immunoreact with fibrinogen in a fibrinogen-GPIIb-IIIa complex. Therefore, the four MAbs tested immunoreact specifically with RIBS on fibrinogen expressed in complex with GPIIb-IIIa but not with RIBS on fibrinogen when complexed with Mac-1.

3. Inhibition of Platelet Aggregation by RIBS Antibodies

Two hundred ul of isolated platelets prepared as described in Example 2 were admixed with 190 ul Tyrode's buffer containing BSA and dextrose (each at 1 mg/ml), fibrinogen (1 mM), calcium (5 mM), and a Fab fragment of MAb 2F10, prepared in Example 2 and present in varying amounts as indicated in Table 4 below. Ten ul of ADP (80 uM in Tyrode's buffer) were then admixed to stimulate platelet aggregation. The admixture was maintained at 37° C. while changes in light transmission of the admixture were monitored over time using a Dual Sample Aggregation Meter (Model DP-247E, Sienco Inc., Morrison, Colo.).

The aggregation meter was calibrated using a solution containing 200 ul PRP and 200 ul Tyrode's buffer to set a low baseline of light transmission at 5 percent for control aggregations and at 10 percent for aggregations in the presence of antibody. The upper limit of 100% light transmission was uniformly set using a mixture of 100 ml PRP and 300 ul Tyrode's buffer.

The results obtained when measuring platelet aggregation inhibition by antibody are shown in Table 4, and are expressed as a percent of light transmission (100%) obtained in the absence of antibody when measured about 3 to 4 minutes after ADP was admixed.

TABLE 4

| INHIBITION OF PLATELET AGGREGATION BY MAB 2F10 | |
|---|---|
| Fab Concentration | Percent Transmission |
| 0 $\mu$M | 100 |
| 0.25 $\mu$M | 79 |
| 0.5 $\mu$M | 62.5 |
| 1.25 $\mu$M | 34.5 |
| 1.87 $\mu$M | 17.5 |

The results in Table 4 show that the MAb 2F10 fragment produced a dose-dependent inhibition of platelet aggregation. Thus, the results indicate the effective dosages useful to inhibit platelet aggregation and processes involving platelet aggregation, such as thrombus formation, when using antibodies of the present invention that immunoreact with a RIBS specific for fibrinogen: GPIIb-IIIa complex.

4. Properties of 2G5 MAb

The monoclonal antibody, designated 2G5, is an IgG of the $\gamma_1$ subclass with a kappa light chain. The production, purification and characterization of the purified antibody have been described elsewhere [Zamarron et al., Thromb Haemost, 64:41 (1990)]. The purified antibody was labeled with biotin-N-hydroxysuccinimide ester (Calbiochem, La Jolla, Calif.) according to standard procedures [Guesdon et al., J Histochem Cytochem, 27:1131 (1979)]and with $^{125}$I by a modified chloramine T procedure [McConahey et al., Int Arch Allergy Apl Immunol, 29:181 (1966)]to a specific activity of approximately 1 $\mu$Ci/$\mu$g. Fab fragments of the antibody were prepared by papain digestion (Sigma Chem. Co., St. Louis, Mo.) at an enzyme to substrate ratio of 1:100 (2/2) for 6 hours at 37° C. [Porter, Biochem J, 730:119 (1959)]. Undigested antibody and Fc fragments were removed by chromatography on protein A Sepharose (Pharmacia, AB, Uppsala, Sweden). Complete digestion of the antibody and the purity of Fab preparation was confirmed by SDS-PAGE. Other monoclonal antibodies to fibrinogen used in this study were derived from mice immunized with fibrin D dimer and were purified from ascites fluid by the same protocol as for 2G5.

Fibrinogen was purified from fresh human blood by differential ethanol precipitation [Doolittle et al., Arch Blochem Biophys, 118:456 (1967)] and was radiolabeled with $^{125}$I as previously described [McConahey et al., Int Arch Allergy Apl Immunol, 29:181 (1966)]. Plasmin digestion of fibrinogen was performed according to described protocols [Veradi et al., *Biochemistry*, 25:519 (1986)]. Fibrinogen (2 mg/ml), in 0.15M NaCl, 0.05M Tris, pH 7.4, containing 5 mM $Ca^{2+}$, was first digested with plasmin, formed by addition of plasminogen (20 μg/ml, final concentration) and streptokinase (Sigma) (200 units/ml, final concentration), for 1 hour at 37° C. The predominant species within this digest, D100 (fragments of approximately 100,000 molecular weight) were isolated by affinity chromatography on an 2G5 column (see below). Additional digestion was performed by dialyzing the sample into the Tris buffer containing 5 mM EGTA {[ethylene-bis (oxyethylenenitrilo)]tetraacetic acid} instead of 5 mM $Ca^{2+}$, and incubating with the plasminogen/streptokinase mixture for 4 hours at 37° C. For selected experiments, the isolated D100 was further digested in the absence of $Ca^{2+}$ with plasmin for 24 hours at 37° C., supplemented with a second addition of plasmin after 8 hours. Proteolysis was terminated by the addition of trasylol (FBA Pharmaceutical, New York, N.Y.) (200 kallikrein inhibitory units/ml).

5. Platelet Binding Studies

Platelets were isolated from fresh human blood by differential centrifugation followed by gel filtration on Sepharose 2B in divalent ion-free Tyrode's buffer, pH 7.3, containing 0.1% bovine serum albumin [Marguerie et al., *J Biol Chem*, 255:154 (1980)]. Binding of the antibody to platelets was performed as follows. Platelets were suspended at $1 \times 10^8$/ml in a divalent ion-free Tyrode's buffer. $CaCl_2$, at a 1 mM final concentration, and the stimulus, 10 μM ADP or 0.5 units/ml α-thrombin, were added to the platelets. When thrombin was used as the stimulus, 30 nM D-phenylalanyl-L-prolyl-arginine ketone (Calbiochem) was added 5 minutes after the addition of thrombin to inactivate the enzyme. $^{125}$I-labeled antibody was then added at a 0.1M final concentration, and binding was measured in the absence or presence of 1 μM fibrinogen. In parallel experiments, $^{125}$I-fibrinogen binding to the cells was measured with the ligand at 0.3 μM as described [Marguerie et al., *J Biol Chem*, 255:154 (1980)]. The platelet-bound ligands were separated from the free ligands by centrifugation of 50 μl aliquots of the reaction mixture through 20% sucrose, and the molecules of ligand bound were calculated based on their specific activity.

6. Platelet Binding Studies

Platelets ($1 \times 10^8$/ml) were stirred at 37° C. in the presence of human fibrinogen (0.3 μM) and $CaCl_2$ (1 mM). Different. concentrations (from 0 to 2 μM) of 2G5, its Fab fragments or a subclass matched control antibody were then added, and aggregation was initiated by the addition of 10 μM ADP. Aggregation was monitored as a change in light transmission through the platelet suspension using a dual sample aggregometer (Sienco, Inc., Morrison, Colo.).

7. Enzyme-linked Immunoabsorbent Assay (ELISA).

Polyvinyl microtiter wells were coated with 100 μl protein at a concentration of 2 μg/ml overnight at 4° C. The plates were postcoated with PBS (0.25M NaCl, 0.01M phosphate buffer, pH 7.3) containing 1% bovine serum albumin, then washed with PBS-0.05% Tween 20 and incubated for 2 hours with the antibody in either an unlabeled or a biotinylated form. Plates were then extensively washed with the PBS-Tween 20 and incubated with a second antibody or avidin, conjugated to alkaline phosphatase (Calbiochem), for 1 hour. After washing, binding was quantitated using the substrate p-nitrophenylphosphate and measuring the absorbance at 405 nm. When competition experiments were performed, the competitor was incubated for 15 minutes at 22° C. with the antibody prior to addition to the wells of the microtiter plates.

8. Peptide Synthesis and Protein Sequencing

Peptides corresponding in sequence to segments of the fibrinogen gamma chain were prepared by solid phase synthesis on an Applied Biosystems model 430 peptide synthesizer (Foster City, Calif.) using phenylacetamidomethyl resins and t-butoxycarbonyl amino acids, purchased from Applied Biosystems. The peptides were analyzed for homogeneity by HPLC using a C18μ Bondapak column with a linear gradient of acetonitrile in 0.1% trifluoroacetic acid and were found to be >85% homogeneous. The amino acid compositions of the peptides were determined on 24 hour hydrolysates in 6N HCl, and the results were consistent with theoretical yields.

Protein sequences were determined for selected bands identified by Coomassie blue staining of SDS-PAGE. The bands of interest were excised from the gels and subjected to $NH_2$-terminal sequencing directly in a gas phase sequenator (Applied Biosystems model 475A) as described [Matsudaira, *J Biol Chem*, 262:10035 (1987)]. The alignments of amino acid sequences of the individual chains of human, bovine and rat fibrinogen were obtained from Rixon et al., *Biochemistry* 22:3237 (1983); Chung et al., *Biochemistry* 22:3244 (1983); Chung et al., *Biochemistry* 22:3250 (1983); Crabtree et al., *Cell* 31:159 (1982) and GENBANK database.

9. Analytical Procedures

Affinity chromatography on 2G5 was performed by coupling the purified antibody to CNBr-activated Sepharose 4B (Pharmacia) according to the manufacturer's instructions. The degree of substitution was 1 mg of antibody bound per ml of settled gel. Affinity chromatography was performed on a $1.1 \times 4.5$ cm column equilibrated in PBS-0.04% azide at 22° C. Sample was applied to the column, and bound material was eluted with 1M ammonium hydroxide (pH 11.5). SDS-PAGE was performed on vertical slab gels in the buffer system of Laemmli [Laemli, *Nature*, 227:280 (1970)]. For Western immunoblot analyses, protein samples were resolved by SDS-PAGE and electrophoretically transferred to Immobilon PVDF membranes (Millipore, Bedford, Mass.). Transfers were probed with the antibody in a biotinylated form (5 μg/ml), and reactions were visualized with alkaline phosphatase conjugated to avidin (Calbiochem) and the enzyme substrates bromochloroindolyl phosphate and nitro blue tetrazolium (Sigma). Dot blot analyses were performed by applying a drop of the protein solution directly to the Immobilon membrane. Antibody reactivity with the absorbed protein was visualized as described [Zamarron et al., *Thromb Haemost*, 64: 41 (1990)].

10. Discussion of Examples 1-9. Expression of RIBS by Platelet-bound Fibrinogen Recognized by 2G5

In a previous study [Zamarron et al., *Thromb Haemost*, 64:41 (1990)], the 2G5 monoclonal antibody was demonstrated to react with fibrinogen immobilized onto plastic microtiter plates or filter paper but 2G5 did not react with soluble fibrinogen. The initial question posed in the present study was whether the binding of fibrinogen to GPIIb-IIIa, its receptor on the surface of platelets, also exposed the recognized epitope; i.e., whether receptor occupancy induces the conformational changes within the fibrinogen ligand to elicit a RIBS epitope.

FIG. 1 shows the binding of the radiolabeled antibody to washed human platelets under conditions resulting in variable occupancy of GPIIb-IIIa with fibrinogen. Fibrinogen binds minimally to nonstimulated platelets, and the antibody also failed to bind to the cells in the presence or absence of exogenously added fibrinogen. ADP stimulation of the platelets converts GPIIb-IIIa from a latent state to one in which it is competent to bind fibrinogen. Stimulation of the platelets in the absence of fibrinogen induced only a slight increase in antibody binding.

When fibrinogen was present, however, extensive antibody binding to the ADP stimulated cells was observed. The increment in antibody binding to ADP stimulated platelets in the presence of fibrinogen was approximately 17-fold. Under these same experimental conditions using platelets from 3 different donors, this increment was 17.2±2.4-fold. Considering that only 0.1% of the added fibrinogen is platelet-bound in the mixture, the binding of the antibody to cell-bound fibrinogen is highly selective. The recognition of platelet-bound fibrinogen also occurred when the cells were stimulated with a different agonist (thrombin). Thrombin stimulated platelets also bound the antibody in the presence of exogenously added fibrinogen. Modest binding of the antibody to thrombin stimulated platelets was observed even in the absence of added fibrinogen and may reflect the binding of the antibody to endogenous fibrinogen which is secreted and becomes bound to GPIIb-IIIa on the cell-surface [Courtois et al., Eur J Biochem, 159:61 (1986)]. Taken together, these observations indicate that the binding of fibrinogen to GPIIb-IIIa on platelets exposes the epitope recognized by 2G5.

Effect of 2G5 on Platelet Aggregation

Binding of fibrinogen to its platelet receptor is a necessary step for platelet aggregation. In initial studies, the effect of intact 2G5 on this cell-cell interaction was analyzed using washed platelets stimulated with ADP in the presence of added fibrinogen. As indicated in Table 5 below, at a final concentration of 1 μM, 2G5 completely abolished platelet aggregation. Three other antibodies to fibrinogen were tested as controls. Two of these antibodies, anti-Fg-88 and anti-Fg-85, had no effect on platelet aggregation. The third control antibody, anti-Fg-128, also abolished platelet aggregation. The basis for the inhibitory activity of anti-Fg-128 can be ascribed to its inhibition of fibrinogen binding to platelets, i.e., at a 0.6 μM concentration, anti-Fg-128 blocked $^{125}$I-fibrinogen binding.

TABLE 5

Effect of Fibrinogen Antibodies on Platelet Aggregation and Fibrinogen Binding to Platelets

| Antibody | Concentration (μM) | % Inhibition of platelet aggregation | % Inhibition of fibrinogen binding to platelets |
|---|---|---|---|
| 2G5 | 1 | 100 | 0 |
| Anti-Fg-128 | 0.6 | 100 | 81 |
| Anti-Fg-88 | 1 | 0 | ND |
| Anti-Fg-85 | 1 | 0 | ND |

ND = not determined

The effect of 2G5 on platelet aggregation was explored further. Fab fragments of the antibody retained the capacity to inhibit platelet aggregation. The inhibitory activity of the Fab fragments was dose dependent and complete inhibition of this functional response was obtained at a 2 μM concentration of the fragments. The Fab fragments did not interfere with platelet stimulation as indicated by the occurrence of platelet shape change despite the abrogation of the subsequent aggregation response.

Localization of the 2G5 Epitope

The 2G5 epitope has previously been shown to be expressed by the fibrinogen gamma chain and by the high molecular weight ($M_r$=100,000) plasmin degradation product of fibrinogen, D100 [Zamarron et al., Thromb Haemost, 64:41 (1990)]. Thus, the epitope resides within the gamma chain segment of the D domain of fibrinogen. D100 has been shown to exist in two forms, D1A and D1, differing only in the amino-terminal residues of their gamma chain segments. Both of these D100 fragments contain the carboxy-terminus of the gamma chain (residue 411), but D1A begins at gamma 65 whereas D1 begins at gamma 85 [Veradi et al., Biochemistry, 25:519 (1986)].

As an initial step, it was desired to determine whether the recognized epitope depends upon the gamma 65-5 segment. Fibrinogen was digested with plasmin in the presence (digest 1) or absence of $Ca^{2+}$ (digest 2). These digests were subjected to affinity chromatography on immobilized 2G5 to yield fall-through (F1 and F2 from digests 1 and 2, respectively) and bound fractions (B1 and B2) eluting at basic pH. These fractions were analyzed by SDS-PAGE followed by Coomassie blue staining or Western immunoblotting after electrophoretic transfer. Only the highest molecular weight species of D fragments reacted with 2G5 on the affinity column and by immuno-blotting. Although lower molecular weight D fragments of $M_4$=85−91,000 were detected within digest 2, these failed to react with the antibody, verifying the restriction of the epitope to D100. When subjected to SDS-PAGE under reducing conditions, B1 and B2 exhibited similar patterns: a doublet of $M_r$40,000 (the beta and gamma chain remnants) and a single band of $M_r$=14,000 (the alpha chain remnant), consistent with described reports [Varadi et al. Biochemistry 25:519 (1986); Southan et al. J Biol Chem 260: 13095 (1985)].

The $M_r$=40,000 bands were excised from the gels and subjected to NH$_2$-terminal amino acid sequence analysis. The sequences obtained were: AIQLTY and SRKML for the $M_r$=40,000 bands from the B1 and B2 fractions, respectively. Both sequences are found within the fibrinogen gamma chain; the first sequence corresponds to the gamma chain residues 65 to 70 and the second to residues 85 to 89. The sequence DNENV was also present which corresponds to residues 134 to 138 of the fibrinogen beta chain. These results indicate that the epitope recognized by 2G5 does not reside within gamma 65-85. Furthermore, the failure of lower molecular weight D fragments to react with the antibody indicates that the carboxy-terminal aspects of the gamma chain must be intact for epitope expression [Veradi et al., Biochemistry, 25:519 (1986)].

Figure 2A:
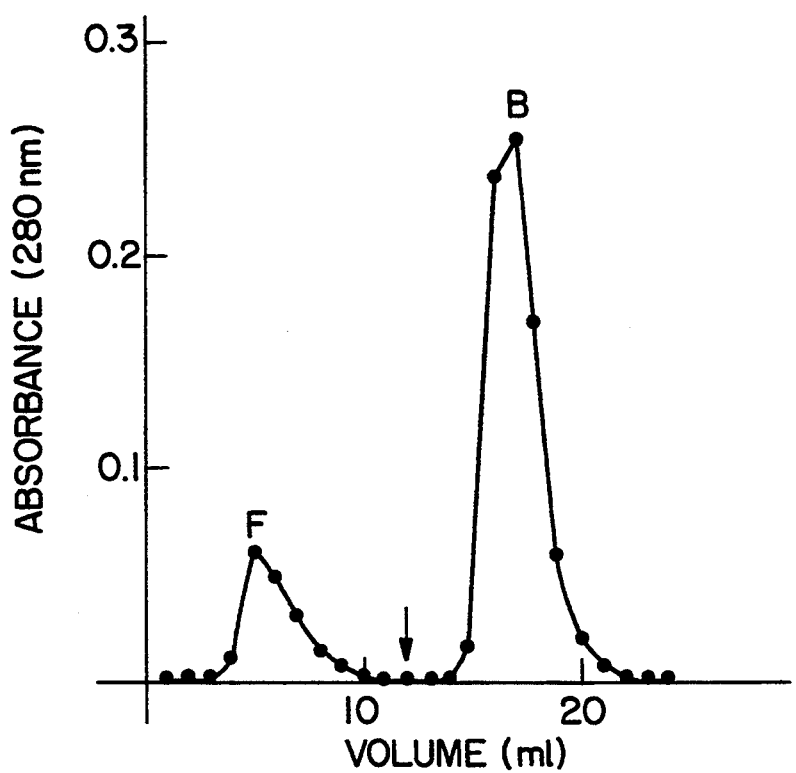
FIGS. 2A and 2B depict isolation of the proteolytic fragments of D100 reactive with MAb 2G5. D100 was digested with plasmin and subjected to affinity chromatography on immobilized 2G5.
Figure 2B:
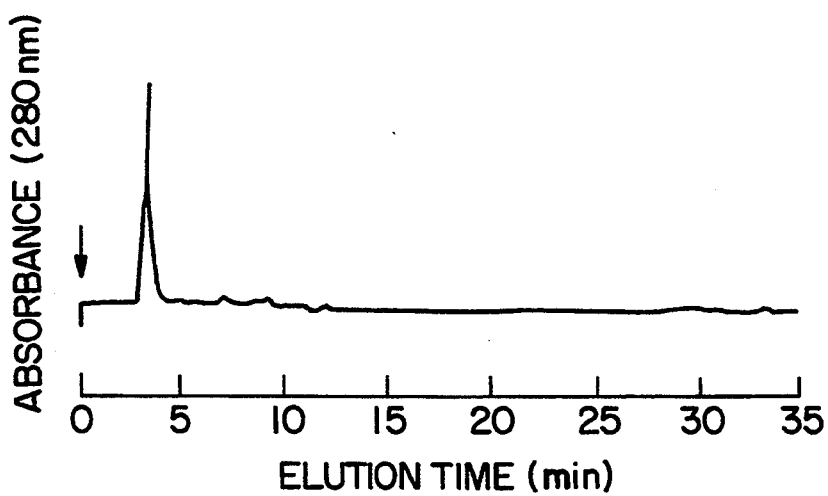

In subsequent experiments, bound fractions from the affinity column were subjected to further digestion with plasmin to ensure that all D100 was degraded to lower molecular weight forms. This digest was then reapplied to the affinity column, and bound material was eluted at basic pH. The chromatogram, monitored at 280 nm, is shown in FIG. 2A. The majority of the material applied to the column was recovered as a bound fraction. Nevertheless, when analyzed by SDS-PAGE (7.5-20% gradient acrylamide gels), no Coomassie blue staining bands were detected. The bound material was then pooled, neutralized with phosphoric acid and fractionated by HPLC on a reverse phase Vydac C18 column. The HPLC profile, monitored at 280 nm, is shown in FIG. 2B. Only one major peak with a retention time of about 4 minutes was detected.

Fractions from different elution times were collected, lyophilized, redissolved in PBS and then tested for their ability to inhibit the binding of 2G5 to immobilized fibrinogen in an ELISA assay. The only fraction (No. 1) with inhibitory activity corresponded to the one eluting from the HPLC column at 4 minutes which contained the 280 nm absorbance peak. As a control, the elution buffer from the affinity column was neutralized with phosphoric acid and applied to the HPLC column. When the fraction equivalent to No. 1 was collected and tested in the ELISA assay, no inhibitory activity was detected. In this assay, the plasmic digest of D100 retained activity, verifying the stability of the epitope RIBS-I during further plasmic digestion.

The selected HPLC fraction was then subjected to NH$_2$-terminal amino acid sequence analysis. Although yields were low (in the 1-2 pmole range), suggesting that some blockage had occurred during the processing the following sequence was obtained: GGTY. These four residues correspond to 351-354 of the fibrinogen gamma chain. These results suggest that the 2G5 resides within a segment extending toward the carboxy-terminus of the gamma chain from residue 351.

Synthesis of the 2G5 Epitope

To verify the localization of the 2G5 epitope to the carboxy terminal region of fibrinogen gamma chain and to further define its structure, a set of overlapping peptides, corresponding to residues 340 to 411 of the gamma chain, were synthesized. The direct binding of the antibody to these peptides was first assessed. Microtiter plates were coated with the peptides (10 μg/ml in PBS), and the binding of 2G5 (50 μg/ml) was determined using an alkaline phosphatase conjugated second antibody. As shown in Table 6 below, the antibody reacted strongly with two of the peptides, P3 and P4. These peptides overlap and correspond to residues 365-383 (P3) and 373-385 (P4) of the gamma chain. A control monoclonal antibody against GPIIb-IIIa failed to react with these two or any of the other peptides. Furthermore, specificity of 2G5 binding to P3 and P4 was demonstrated as the reaction was inhibited with soluble D100 or its further plasmic digest; for P4, the IC50 values for D100 and its plasmic digest were 150 μg/ml and 30 μg/ml, respectively.

In another set of experiments, microtiter plates were coated with affinity-purified D100 and the ability of the synthetic peptides to inhibit the binding of 2G5 to this fragment was assessed. P4 inhibited antibody binding to immobilized D100, whereas P2 had no effect. (P3 behaved anomalously, increasing rather than inhibiting or having no effect on the reaction, possibly due to binding of the P3 peptide to the immobilized fragment.) The inhibitory activity of P4 was very similar to that observed with soluble D100 or its further plasmic digest.

The P4 peptide was also shown to react with 2G5 by affinity chromatography. P4 (1 mg in ml of PBS) was applied to the antibody column and after extensive washing of the column, the bound peptide was eluted at basic pH and its recovery was quantitated. Based on its absorbance at 280 nm, it was estimated that 44 μmoles peptide were bound to the column. Assuming that all 26 μmoles of antibody in the column were fully functional, the recovery of peptide approached the theoretical limit of two moles of peptide bound per mole of antibody. When the P2 peptide was applied to the column under the same conditions, no detectable material was eluted from the column. In addition, when P4 was also applied to an albumin-Sepharose column, no peptide was bound to the column.

Role of Specific Amino Acids and Protein Conformation in Establishing the 2G5 Epitope An analysis of the reactivity of 2G5 with bovine and rat fibrinogen provided insight into the fine structural requirements for the RIBS-I epitope. By dot blot analysis, rat and bovine fibrinogen failed to react with the antibody, when applied to the filter paper at 1 mg/ml, whereas reaction with human fibrinogen was demonstrated in the same analysis at 10 μg/ml.

As shown in Table 7, alignment of the P4 sequence of the gamma chain, Lys373-Lys385, with the corresponding sequences in the rat and bovine fibrinogen gamma chains indicated only single amino acid differences: lysine381 in human fibrinogen is replaced by glutamine in rat fibrinogen, and threonine374 in human fibrinogen is replaced by a serine in bovine fibrinogen.

Peptides corresponding to the rat and bovine gamma chain sequences were synthesized, immobilized on microtiter plates, and their reactivity with the antibody was assessed in an ELISA as;say. Neither the rat nor the bovine peptide reacted with the antibody, whereas its reaction with the human peptide was observed in the same assay (Table 7). An unrelated control antibody failed to give a detectable signal with the human peptide, as well as with the other two peptides in the same assay.

TABLE 6

| | Reactivity of 2G5 MAb with Synthetic Peptides* | | | |
|---|---|---|---|---|
| Peptide | Amino Acid Sequence | Residues | SEQ ID NO | Absorbance at 405 nm |
| P1 | HAGHLNGVYYQGGTYSKA | Fgγ340-57 | 3 | 0.086 |
| P2 | GGTYSKASTPNGYDNGIIWA | Fgγ351-70 | 4 | 0.097 |
| P3 | NGIIWATWKTRWYSMKKTT | Fgγ365-83 | 2 | 0.520 |
| P4 | KTRWYSMKKTTMK | Fgγ373-85 | 1 | 0.624 |
| P5 | YSMKKTTMKIIPFNRLTIG | Fgγ377-95 | 5 | 0.099 |
| P6 | MKIIPFNRLTIGEGQQHL | Fgγ384-402 | 6 | 0.045 |
| P7 | QQHHLGGDKQAGDV | Fgγ398-411 | 7 | 0.071 |

*The reactivity of the 2G5 antibody with the peptides immobilized on microtiter plates, was assessed in an ELISA format. Results are expressed as the absorbance at 405 nm.

TABLE 7

| Reactivity of 2G5 MAb with Homologous Peptides from Human, Rat and Bovine Fibrinogen Gamma Chains | | | |
|---|---|---|---|
| Species | Amino Acid Sequence of Synthetic Peptides | SEQ ID NO | Absorbance at 405 nm* |
| Human | KTRWYSMKKTTMK | 1 | 0.660 |
| Rat | KTRWYSMKQTTMK | 8 | 0.070 |
| Bovine | KSRWYSMKKTTMK | 9 | 0.046 |

*Conditions are the same as employed for the studies reported in Table 6.

The effect of reduction, alkylation and/or denaturation on expression of the 2G5 epitope in human fibrinogen was also analyzed. As assessed by Western immunoblotting, the epitope was maintained when the molecule was denatured with 6M guanidine HCl, reduced with dithiothreitol, or alkylated with iodoacetic acid. In contrast, when fibrinogen was reduced and alkylated in the presence or absence of denaturant, the epitope was no longer detected. In a control experiment, the synthetic P4 peptide was subjected to reduction and alkylation under the same conditions that abrogated the epitope in fibrinogen. When immobilized onto microtiter plates, the reactivity of treated and untreated P4 with 2G5 was the same. Thus, the loss of the RIBS-I epitope in reduced and alkylated fibrinogen appears to arise from changes occurring outside of the linear Lys373-Lys385 sequence.

Discussion

GPIIb-IIIa can exist in multiple conformational states [Plow et al., *Progress in Hemostasis and Throbosis*, Vol. 9 (Coller, B. S., ed), pp. 117–156 (1989)]. Certain of these conformational transitions are induced by platelet agonists which convert GPIIb-IIIa from a latent state to one in which it is competent to bind ligands. Still other conformational transitions are induced by ligand binding to the receptor at; documented by changes in the biophysical and spectral properties of the occupied receptor [Parise et al., *J Biol Chem*, 262:12597 (1987)]and by the exposure of LIBS epitopes [Frelinger et al., *J Biol Chem*, 263:12397 (1988); Frelinger et al., *J Biol Chem*, 265:6346 (1990)]. The expression of RIBS epitopes indicates that the ligand also undergoes conformational changes upon binding to the receptor and attests to the dynamic nature of the post-receptor occupancy events. Just as ligand binding has now been shown to elicit multiple LIBS epitopes from throughout GPIIb-IIIa [Frelinger et al., *J Biol Chem*, 265:6346 (1990)], it is also reasonable to hypothesize that several distinct RIBS epitopes may be elicited when fibrinogen is bound to this receptor. 2G5 and 9F9 [Abrams et al., *Blood*, 75:128 (1990)]may represent two distinct examples of RIBS epitopes. Logical extensions of the RIBS hypothesis include the possibilities that these epitopes may be induced: 1) when other ligands, such as von Willebrand factor or fibronectin, bind to GPIIb-IIIa; 2) when fibrinogen binds to other integrins (such as $\alpha_v\beta_3$ [Cheresh et al., *Cell*, 58:945 (1989)] or MAC-1 [Altieri et al., *J Cell Biol*, 107:1893 (1988)]or non-integrin receptors [Levesque et al., *J Biol Chem*, 265:328 (1990)]; and 3) when ligands bind to other integrin or non-integrin receptors. Initial support for such predictions can be derived from the demonstration that LIBS epitopes are elicited by multiple ligands binding to GPIIb-IIIa and by ligand binding to integrins other than GPIIb-IIIa [Frelinger et al., *J Biol Chem*, 265:6346 (1990); O'Toole et al., *Cell Regul.*, 1:883 (1990)].

The RIBS recognized by 2G5 is the first RIBS epitope to be localized. The P3 peptide, corresponding to gamma chain residues 365–383, and the P4 peptide, corresponding to gamma chain residues 373–385, both bound to 2G5. Thus, at least part of the epitope must reside within residues 373–383 of the gamma chain. As the P5 peptide, which corresponds to residues 377–395, did not react with the antibody, the four residues (373)KTRW(376) must be a key element in defining the 2G5 epitope.

A single conservative substitution of a threonine to a serine at the position corresponding to residue 374 is sufficient to abolish antibody reactivity. The proteolytic fragmentation analyses restricted this epitope to the region between residue 351 and the carboxy-terminus of the gamma chain and provide independent corroboration of the localization. Despite the importance of the KTRW residues of gamma 373–376 for antibody reactivity, the 2G5 epitope shows considerable more complexity. An amino acid substitution at position 381 also abrogated the epitope. In addition, the secondary and tertiary structure of fibrinogen contributes significantly to the epitope. Thus, reduction and alkylation of fibrinogen also destroyed the 2G5 epitope, even though exposure of the P4 peptide to the reducing and alkylating agents failed to effect reaction of the antibody with the peptide. These results indicate that at least one of the secondary, tertiary and quaternary structure of fibrinogen must be stabilizing the gamma 373–385 linear sequence within a conformation that is reactive with the antibody or that a second region of fibrinogen brought into proximity by conformational folding of the molecule may also be part of the epitope.

Secondary structural predictions [Chou et al., *Biochemistry*, 13:222 (1974)]suggest a transition from an $\alpha$-helix to a $\beta$-sheet begins at residue Lys373 and that the gamma chain again begins to assume a helical conformation at Gly395. Such transitions in secondary structure often form epitopes in protein molecules [Todd et al., *Trends Biochem Sci*, 7:212 (1982)]. In addition, in an hydropathy plot [Hopp et al., *Natl Acad Sci USA*, 78:3824 (1981)], this region is predicted to be hydrophilic in character, thus fitting this criterion for antigenicity [Berzofsky, Science, 229:932 (1985). The presence of aromatic amino acids within a hydrophilic stretch of amino acids is an additional determinant of antigenicity in peptides [Appel et al., *J Immunol*, 144:976 (1990)], and gamma 373–383 contains both a tryptophan and a tyrosine residue. Therefore, gamma 373–385 has a high probability of forming an epitope within the fibrinogen molecule. Nevertheless, this region is not accessible to the 2G5 antibody in the native molecule. In models of fibrinogen based upon electron microscopy [Weisel et al., *Science*, 230:1388 (1985)], it appears that this region of the gamma chain resides within an independent globular domain, and this organization may constrain access of the antibody to the epitope. This interpretation has certain implications regarding a general strategy for producing RIBS antibodies. It suggests that an altered form of the ligand, such as induced by mild denaturation on limited proteolysis, may provide a format of the immunogen for eliciting anti-RIBS. In the case of the 2G5 RIBS, a proteolytic fragment of fibrinogen elicited the antibody.

The carboxy-terminal region of the gamma chain of fibrinogen plays an important role in fibrin polymerization as evidenced by the localization of single amino acid substitutions within the gamma 275–330 region of fibrinogens with polymerization defects [Terukina et al., *Blood*, 74:2681 (1989); Reber et al., *Thromb Haemost*, 56:401 (1986); Reber et al., *Blood*, 67:1751 (1986); Bantia et al., *Blood*, 75:1659 (1990); Bantia et al., *Blood*, 76:2279 (1990)]. In addition, the studies by Varadi and Scheraga [Veradi et al., *Biochemistry*, 25:519 (1986)]suggest that the region gamma 356–405 is involved in fibrin polymerization although protein conformation plays a crucial role in mediating this function [Cierniewski et al., *J Biol Chem*, 261:9116 (1986)].

The capacity of the 2G5 antibody to inhibit both platelet aggregation and fibrin polymerization [Zamarron et al., Thromb Haemost, 64:41 (1990)] suggests a previously unrecognized linkage between the two functions of the fibrinogen molecule. In a simplest model for platelet aggregation, a single fibrinogen molecule, by virtue of its dimeric structure and its multiple GPIIb-IIIa interactive sites, directly bridges between receptors on adjacent platelets, thereby inducing their aggregation. Such a direct bridging model fails to explain why certain platelet preparations (formaldehyde-fixed [Peerschke et al., Blood, 57:663 (1981)]or refractory platelets [Peerschke, J Lab Clin Med, 106:111 (1985)]) fail to aggregate despite their normal binding of fibrinogen to GPIIb-IIIa. These inconsistencies with the direct bridging models suggests that post-receptor occupancy events may be necessary for platelet aggregation.

Although the present invention is described in some detail by way of illustration and example for purposes of clarity, it will be obvious that certain modifications can be practiced within the scope of the appended claims.

What is claimed is:

1. A polypeptide comprising up to about 40 amino acid residues including an amino acid residue sequence having the formula:

Lys-Thr-Arg-Trp-Tyr-Ser-Met-Lys-Lys-Thr-Thr-Met-Lys (SEQ ID NO 1).

2. A polypeptide composition comprising a polypeptide as in claim 1 and a pharmaceutically acceptable carrier or excipient.

3. The polypeptide of claim 1, wherein said polypeptide is immobilized on a solid support.

4. The polypeptide of claim 1 having the formula:

Asn-Gly-Ile-Ile-Trp-Ala-Thr-Trp-Lys-Thr-Arg-Trp-Tyr-Ser-Met-Lys-Lys-Thr-Thr (SEQ ID NO 2).

5. A polypeptide comprising up to about 20 amino acid residues including an amino acid residue sequence selected from the group consisting of:

Lys-Thr-Arg-Trp-Tyr-Ser-Met-Lys-Lys-Thr-Thr-Met-Lys (SEQ ID NO 1);

and

Asn-Gly-Ile-Ile-Trp-Ala-Thr-Trp-Lys-Thr-Arg-Trp-Tyr-Ser-Met-Lys-Lys-Thr-Thr (SEQ ID NO 2)

6. The polypeptide of claim 5 having the formula:

Lys-Thr-Arg-Trp-Tyr-Ser-Met-Lys-Lys-Thr-Thr-Met-Lys (SEQ ID NO 1).

7. A polypeptide composition comprising a polypeptide as in claim 5 and a pharmaceutically acceptable carrier or excipient.

8. A polypeptide comprising up to about 40 amino acid residues including an amino acid residue sequence corresponding to the formula:

Asn-Gly-Ile-Ile-Trp-Ala-Thr-Trp-Lys-Thr-Arg-Trp-Tyr-Ser-Met-Lys-Lys-Thr-Thr (SEQ ID NO 2).

9. A polypeptide composition comprising a polypeptide as in claim 8 and a pharmaceutically acceptable carrier or excipient.

10. A polypeptide comprising p to about 30 amino acid residues including an amino acid residue sequence selected from the group consisting of:

Lys-Thr-Arg-Trp-Tyr-Ser-Met-Lys-Lys-Thr-Thr-Met-Lys (SEQ ID NO 1);

and

Asn-Gly-Ile-Ile-Trp-Ala-Thr-Trp-Lys-Thr-Lys-Thr-Arg-Trp-Tyr-Ser-Met-Lys-Lys-Thr-Thr (SEQ ID NO 2).

11. A polypeptide composition comprising a polypeptide as in claim 10 and a pharmaceutically acceptable carrier or excipient.

12. A method for detecting the presence of an anti-RIBS antibody in a solution containing said antibody, said method comprising:

subjecting said solution to a polypeptide immobilized on a surface, said polypeptide comprising up to about 40 amino acid residues including an amino acid residue sequence having the formula:

Lys-Thr-Arg-Trp-Tyr-Ser-Met-Lys-Lys-Thr-Thr-Met-Lys (SEQ ID NO 1);

maintaining the antibody in contact with the polypeptide for a sufficient time to form an antibody-polypeptide immunocomplex; and determining the presence of immunocomplex formed and thereby the presence of antibody in solution.

13. The method of claim 12, wherein said polypeptide comprises up to about 20 amino acid residues including an amino acid residue sequence selected from the group consisting of:

Lys-Thr-Arg-Trp-Tyr-Ser-Met-Lys-Lys-Thr-Thr-Met-Lys (SEQ ID NO 1);

and

Asn-Gly-Ile-Ile-Trp-Ala-Thr-Trp-Lys-Thr-Arg-Trp-Tyr-Ser-Met-Lys-Lys-Thr-Thr (SEQ ID NO 2).

* * * * *

UNITED STATES PATENT AND TRADEMARK OFFICE
CERTIFICATE OF CORRECTION

PATENT NO.   :   5,372,933
DATED        :   December 13, 1994
INVENTOR(S)  :   Zamarron, Plow, Ginsberg It is certified that error appears in the above-identified patent and that said Letters Patent is hereby corrected as shown below:

In column 38, in claim 10, line 22, delete "p" and insert instead -- up --.

In Column 38, in claim 10, lines 30-31, kindly delete "Asn-Gly-Ile-Ile-Trp-Ala-Thr-Trp-Lys-Thr-Lys-Thr-Arg-Trp-Tyr-Ser-Met-Lys-Lys-Thr-Thr" and insert instead -- Asn-Gly-Ile-Ile-Trp-Ala-Thr-Trp-Lys-Thr-Arg-Trp-Tyr-Ser-Met-Lys-Lys-Thr-Thr --.

Signed and Sealed this

Twenty-eight Day of March, 1995

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:1:

```
Lys Thr Arg Trp Tyr Ser Met Lys Lys Thr Thr Met Lys
1               5                   10
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:2:

```
Asn Gly Ile Ile Trp Ala Thr Trp Lys Thr Arg Trp Tyr Ser Met Lys
1               5                   10                  15
Lys Thr Thr
```

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:3:

```
His Ala Gly His Leu Asn Gly Val Tyr Tyr Gln Gly Gly Thr Tyr Ser
1               5                   10                  15
Lys Ala
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:4:

Gly Gly Thr Tyr Ser Lys Ala Ser Thr Pro Asn Gly Tyr Asp Asn Gly
1               5                   10                  15
Ile Ile Trp Ala
            20

( 2 ) INFORMATION FOR SEQ ID NO:5:

( i ) SEQUENCE CHARACTERISTICS:
( A ) LENGTH: 19 amino acids
( B ) TYPE: amino acid
( D ) TOPOLOGY: linear ( i i ) MOLECULE TYPE: peptide ( i i i ) HYPOTHETICAL: NO ( x i ) SEQUENCE DESCRIPTION: SEQ ID NO:5:

Tyr Ser Met Lys Lys Thr Thr Met Lys Ile Ile Pro Phe Asn Arg Leu
1               5                   10                  15
Thr Ile Gly ( 2 ) INFORMATION FOR SEQ ID NO:6:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( i i i ) HYPOTHETICAL: NO ( x i ) SEQUENCE DESCRIPTION: SEQ ID NO:6:

Met Lys Ile Ile Pro Phe Asn Arg Leu Thr Ile Gly Glu Gly Gln Gln
1               5                   10                  15
His Leu ( 2 ) INFORMATION FOR SEQ ID NO:7:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i i i ) HYPOTHETICAL: NO ( x i ) SEQUENCE DESCRIPTION: SEQ ID NO:7:

Gln Gln His His Leu Gly Gly Asp Lys Gln Ala Gly Asp Val
1               5                   10

( 2 ) INFORMATION FOR SEQ ID NO:8:

( i ) SEQUENCE CHARACTERISTICS:
( A ) LENGTH: 13 amino acids
( B ) TYPE: amino acid
( D ) TOPOLOGY: linear ( i i ) MOLECULE TYPE: peptide ( i i i ) HYPOTHETICAL: NO ( x i ) SEQUENCE DESCRIPTION: SEQ ID NO:8:

Lys Thr Arg Trp Tyr Ser Met Lys Gln Thr Thr Met Lys (2) INFORMATION FOR SEQ ID NO:9:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:9:

Lys Ser Arg Trp Tyr Ser Met Lys Lys Thr Thr Met Lys
    1         5                  10